US009284574B2

(12) United States Patent
Alt et al.

(10) Patent No.: US 9,284,574 B2
(45) Date of Patent: Mar. 15, 2016

(54) RAG-BASED SELECTION METHODS FOR IMPROVING APHID RESISTANCE IN SOYBEANS

(71) Applicant: PIONEER HI-BRED INTERNATIONAL, INC., Johnston, IA (US)

(72) Inventors: Jessie L. Alt, Madrid, IA (US); Julian M. Chaky, Urbandale, IA (US); Molly Ryan-Mahmutagic, Waukee, IA (US); John B. Woodward, Ankey, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 357 days.

(21) Appl. No.: 13/724,154

(22) Filed: Dec. 21, 2012

(65) Prior Publication Data

US 2013/0174295 A1   Jul. 4, 2013

Related U.S. Application Data

(60) Provisional application No. 61/581,151, filed on Dec. 29, 2011.

(51) Int. Cl.
| | |
|---|---|
| *C12Q 1/68* | (2006.01) |
| *A01H 1/04* | (2006.01) |
| *C12N 15/82* | (2006.01) |
| *A01H 1/00* | (2006.01) |
| *A01H 5/10* | (2006.01) |

(52) U.S. Cl.
CPC .............. *C12N 15/8286* (2013.01); *A01H 1/00* (2013.01); *A01H 1/04* (2013.01); *A01H 5/10* (2013.01)

(58) Field of Classification Search
None
See application file for complete search history.

(56) References Cited

U.S. PATENT DOCUMENTS

| | | | |
|---|---|---|---|
| 7,994,389 B2 | 8/2011 | Hill et al. | |
| 8,227,662 B2 | 7/2012 | Wang et al. | |
| 8,530,723 B2 | 9/2013 | Yu et al. | |
| 2010/0083396 A1* | 4/2010 | Hill et al. | ..................... 800/265 |
| 2012/0174246 A1 | 7/2012 | Chaky et al. | |

FOREIGN PATENT DOCUMENTS

| | | |
|---|---|---|
| WO | WO 2008/067043 A2 | 6/2008 |
| WO | WO 2009/021153 A2 | 2/2009 |
| WO | WO 2011/097492 A1 | 8/2011 |

OTHER PUBLICATIONS

Schmutz et al., 2010, Nature 463: 178-183, corrigendum in Nature 465: 120.*
Glycine max clone gmw1-42i18, GenBank Accession No. AC144537, published Sep. 17, 2010.*
Kim, 2009, PhD thesis, University of Illinois at Urbana-Champaign, pp. 1-132.*
Zhang et al., 2010, Theor. Appl. Genet. 120: 1183-1191.*
Auclair J.L., "Host plant resistance," In Aphids: Their biology, natural enemies, and control. A.K. Minks and P. Harrewijn (ed.). Elsevier, New York. vol. C (1989) 225-265.
Choi I.-Y., et al. "A Soybean Transcript Map: Gene Distribution, Haplotype and Single-Nucleotide Polymorphism Analysis" Genetics. 176 (2007) 685-696.
Clark A.J. and Perry K.L. "Transmissibility of field isolates of soybean viruses by Aphis glycines" Plant Dis. 86 (2002) 1219-1222.
Cregan P.B., et al. "An Integrated Genetic Linkage Map of the Soybean Genome" Crop Science. 39 (1999) 1464-90.
Dogiment C., et al. "Host plant resistance to aphids in cultivated crops: Genetic and molecular bases, and interactions with aphid populations" C.R. Biologies. 333 (2010) 566-573.
Harrewijn P. and Minks A.K. "Host plant resistance," In Aphids: Their biology, natural enemies, and control. A.K. Minks and P. Harrewijn (ed.). Elsevier, New York. vol. C (1989) 267-272.
Hartman G.L., et al. "Occurrence and distribution of Aphis glycines on soybeans in Illinois in 2000 and its potential control" Plant Health Progress. (Feb. 5, 2001) available at plantmanagementnetwork.org/phpldefault.asp.
Hill C.B., et al. A new soybean aphid (Hemiptera: Aphididae) Biotype Identified. Journal of Economic Entomology. 103 (2010) 509-515.
Hill C.B., et al. "Resistance of Glycine species and various cultivated legumes to the soybean aphid (Homoptera: Aphididae)" J. Economic Entomology. 97(3) (2004) 1071-1077.
Hill C.B., et al. "Resistance to the Soybean Aphid in Soybean Germplasm" Crop Science. 44 (2004) 98-106.
Hill J.H. "First Report of Transmission of Soybean mosaic virus and Alfalfa mosaic virus by Aphis glycines in the New World" Plant Dis. 85 (2001) 561.
Iwaki M., et al. "A persistent aphid borne virus of soybean, Indonesian Soybean dwarf virus transmitted by Aphis glycines" Plant Dis. 64 (1980) 1027-1030.
Jun T.-H., et al. "Genetic mapping revealed two loci for soybean aphid resistance in PI 567301B" Theor. Appl. Genet. 124 (2012) 13-22.
Kim K.S., et al. "Fine mapping of the soybean aphid resistance gene Rag1 in soybean" Theor. Appl. Genet. 120 (2010) 1063-1071.
Kim K.S., et al. "Fine mapping of the soybean aphid-resistance gene Rag2 in soybean PI 200538" Theor. Appl. Genet. 121 (2010) 599-610.
Li Y., et al. "Effect of three resistant soybean genotypes on the fecundity, mortality, and maturation of soybean aphid (Homoptera: Aphididae)" J. Economic Entomology. 97 (2004) 1106-1111.

(Continued)

*Primary Examiner* — David T Fox
*Assistant Examiner* — Bratislav Stankovic

(57) ABSTRACT

This invention relates to methods of improving resistance to aphids in soybean plants, as well as methods for identifying and/or selecting soybean plants or germplasm that display improved resistance to one or more biotypes of soybean aphid. In certain examples, the method comprises selecting a first and second soybean plant or germplasm, each of which has a different favorable Rag1, Rag2, or Rag3, allele, haplotype, or marker profile, and crossing those first and second soybean plants to produce a progeny plant with improved soybean aphid resistance. This invention further relates to markers, primers, probes, kits, systems, etc., useful for carrying out the methods described herein.

12 Claims, 3 Drawing Sheets

(56) References Cited

OTHER PUBLICATIONS

Luginbill J.P., "Developing resistant plants—The ideal method of controlling insects," USDA, ARS. Prod. Res. Rep. 111, USGPO, Washington, D.C. (1969).

Meng F., et al. "QTL underlying the resistance to soybean aphid (Aphis glycines Matsumura) through isoflavone-mediated antibiosis in soybean cultivar 'Zhongdou 27'" Theor. Appl. Genet. 123 (2011) 1459-1465.

Ostlie K., "Managing soybean aphid" University of Minnesota Extension Service. (Oct. 2, 2002) available at soybeans.umn.edu/crop/insects/aphid/aphid~publicationmanagingsba.htm.

Patterson J. and Ragsdale D. "Assessing and managing risk from soybean aphids in the North Central States," (Apr. 11, 2002).

Rouf Mian M.A., et al. "Genetic linkage mapping of the soybean aphid resistance gene in PI 243540" Theor. Appl. Genet. 117 (2008): 955-962.

Sama S., et al. "Varietal Screening for resistance to the aphid, Aphis glycines, in soybean" Research Reports. (1974) 171-172.

Schmutz J., et al. "Genome sequence of the palaeopolyploid soybean" Nature. 463 (2010) 178-183.

Sun Z., et al. "Study on the uses of aphid-resistant character in wild soybean. I. Aphid-resistance performance of F2 generation from crosses between cultivated and wild soybeans" Soybean Genet. News. 17 (1990) 43-48.

Univeristy of Illinois. "U of I researchers identify new soybean aphid biotype" Scientific Centric. (Mar. 30, 2010) University of Illinois at Urbana-Champaign.

Wang X.B., et al. "A study on the damage and economic threshold of the soybean aphid at the seedling stage," Plant Prot. (China) 20 (1994) 12-13.

Wang X.B., et al. "Study on the effects of the population dynamics of soybean aphid (Aphis glycines) on both growth and yield of soybean," Soybean Sci. 15 (1996) 243-247.

Zhang G., et al. "A novel locus for soybean aphid resistance" Theor. Appl. Genet. 120 (2010) 1183-1191.

Brace R.C. and Fehr W.R. "Impact of Combining the Rag1 and Rag2 Alleles for Aphid Resistance on Agronomic and Seed Traits of Soybean" Crop Science. 52 (2012) 2070-2074.

Hill C.B., et al. "Resistance and Virulence in the Soybean-Aphis glycines Interaction" Euphytica. 186 (2012) 635-646.

Wiarda S.L., et al. "Soybean Aphis (Hemiptera: Aphididae) Development on Soybean With Rag1 Alone, Rag2 Alone, and Both Genes Combined" J. Econ. Entomol. 105(1) (2012) 252-258.

Zhang G., et al. "Molecular Mapping of Soybean Aphid Resistance Genes in PI 567541B" Theor. Appl. Genet. 118 (2009) 473-482.

International Search Report and Written Opinion in PCT/US2012/071328, mailed Mar. 20, 2013.

* cited by examiner

FIG. 1A

| SNP name/Locus name | Linkage group | cM position |
|---|---|---|
| BARC-031399-07088 | M | 30.33 |
| BARC-013845-01256 | M | 30.36 |
| Satt540 | M | 32.17 |
| BARC-015945-02020 | M | 32.83 |
| Sat_435 | M | 32.97 |
| Satt567 | M | 33.84 |
| Bng222_1 | M | 36.51 |
| RGA_2b | M | 37 |
| R079_1 | M | 37.81 |
| Satt435 | M | 38.43 |
| BARC-028455-05920 | M | 38.68 |
| BARC-022289-04309 | M | 39.09 |
| BARC-039383-07310 | M | 39.44 |
| A060_2 | M | 39.73 |
| BARC-039195-07466 | M | 41.75 |
| BARC-014705-01623 | M | 44.81 |
| BARC-028243-05801 | M | 45.05 |
| A131_1 | M | 45.77 |
| BARC-007573-00060 | M | 47.37 |
| Satt463 | M | 47.45 |
| Sat_244 | M | 47.49 |
| BARC-012945-00406 | M | 47.5 |
| BARC-032703-09018 | M | 49.02 |
| Sat_253 | M | 49.86 |
| BARC-016783-02329 | M | 50.83 |
| Satt245 | M | 51.94 |
| Satt220 | M | 53.32 |
| A946_2 | M | 55.13 |
| A584_3 | M | 55.4 |
| Sat_258 | M | 56.83 |
| BARC-032007-07237 | M | 57.14 |
| BARC-044899-08837 | M | 57.65 |
| Satt626 | M | 57.69 |
| Satt323 | M | 57.71 |
| Sat_003 | M | 58.35 |
| Satt702 | M | 58.71 |
| BARC-028235-05800 | M | 59.08 |
| L204_4 | M | 59.18 |
| Satt536 | M | 60.1 |

Rag 1 Interval (Satt540 through BARC-016783-02329)

FIG. 1B

| SNP name/Locus name | Linkage group | cM position |
|---|---|---|
| A757_1 | F | 65.34 |
| A186_1 | F | 66.36 |
| Sat_234 | F | 66.66 |
| L063_1 | F | 66.99 |
| BARC-007730-00067 | F | 67.64 |
| L28831 | F | 67.66 |
| BARC-017133-02218 | F | 67.67 |
| BARC-010137-00527 | F | 68.11 |
| BARC-010279-00575 | F | 68.11 |
| Sat_154 | F | 68.33 |
| BARC-008001-00154 | F | 68.85 |
| BARC-031461-07098 | F | 68.85 |
| BARC-025897-05144 | F | 68.85 |
| K644_1 | F | 68.85 |
| Satt334 | F | 68.96 |
| BARC-007567-00030 | F | 69.65 |
| BARC-022043-04271 | F | 69.85 |
| BARC-029823-06424 | F | 69.9 |
| Rpg1 | F | 70.04 |
| R045_1 | F | 70.04 |
| B212_1 | F | 71.08 |
| BARC-017917-02451 | F | 71.8 |
| BARC-030853-06954 | F | 72.28 |
| BARC-007567-00027 | F | 72.46 |
| BARC-014579-01586 | F | 72.46 |
| BARC-018521-02929 | F | 72.46 |
| Satt510 | F | 72.46 |
| BARC-013633-01184 | F | 72.95 |
| BARC-015903-02010 | F | 73.93 |
| BARC-010501-00678 | F | 74.21 |
| BARC-029683-06313 | F | 74.21 |
| K007_2 | F | 74.21 |
| Sct_033 | F | 74.21 |
| Sat_317 | F | 74.54 |
| BARC-015435-01966 | F | 75.79 |
| Sat_120 | F | 76.52 |
| BARC-030359-06858 | F | 77.98 |
| Satt335 | F | 77.98 |
| A245_1 | F | 80.64 |
| Satt362 | F | 82.35 |
| A708_1 | F | 83.87 |
| BARC-027502-06598 | F | 85.91 |
| BARC-032717-09021 | F | 85.91 |
| Sat_375 | F | 85.91 |

Rag2 Interval: Satt334 (68.96) to Sat_317 (74.54)

FIG. 1C

| SNP name/Locus name | Linkage group | cM position |
|---|---|---|
| Sat_339 | J | 27.82 |
| E107_1 | J | 28.53 |
| BARC-016775-02322 | J | 28.77 |
| K384_1 | J | 31.24 |
| A450_1 | J | 32.54 |
| B166_1 | J | 33.18 |
| BARC-031195-07010 | J | 33.78 |
| BARC-028307-05823 | J | 33.88 |
| BARC-031951-07227 | J | 34.1 |
| RGA_6d | J | 35.46 |
| BARC-018889-03033 | J | 36.84 |
| p40_2_2 | J | 37.33 |
| Satt693 | J | 37.71 |
| Bng044_1 | J | 38.16 |
| BLT049_4 | J | 38.45 |
| BARC-028159-05778 | J | 38.87 |
| Sat_370 | J | 39.23 |
| Sct_065 | J | 39.81 |
| Satt654 | J | 40.35 |
| Satt406 | J | 41.05 |
| BARC-010251-00569 | J | 41.32 |
| BARC-041381-07975 | J | 41.36 |
| BARC-032391-08958 | J | 41.53 |
| Satt414 | J | 41.67 |
| Satt132 | J | 42.15 |
| BARC-015951-02021 | J | 42.2 |
| Satt596 | J | 42.59 |
| Scaa003 | J | 42.88 |
| BARC-044047-08593 | J | 43.06 |
| BARC-025801-05075 | J | 43.09 |
| Sat_259 | J | 43.25 |
| BARC-017157-02226 | J | 43.35 |
| Satt686 | J | 43.42 |
| Satt456 | J | 43.88 |
| L050_6 | J | 43.99 |
| Sat_412 | J | 44.02 |
| Sct_193 | J | 44.27 |
| Sat_151 | J | 44.28 |
| L216_2 | J | 44.53 |
| Satt529 | J | 44.59 |
| BARC-022261-04297 | J | 44.82 |
| Satt622 | J | 45.1 |
| Sat_165 | J | 45.12 |
| BARC-019807-04396 | J | 45.15 |

Rag3 Interval (Sat_339 through Sct_065)

RAG-BASED SELECTION METHODS FOR IMPROVING APHID RESISTANCE IN SOYBEANS

FIELD OF THE INVENTION

This invention relates to methods of improving resistance to aphids in soybean plants, as well as methods for identifying and/or selecting soybean plants or germplasm that display improved resistance to one or more biotypes of soybean aphid.

BACKGROUND

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications. Soybeans are also vulnerable to more than one hundred different pathogens, with some pathogens having disastrous economic consequences. One important soybean pathogen is the soybean aphid, which can severely impact yield. Despite a large amount of effort expended in the art, commercial soybean crops are still largely susceptible to aphid infestation.

A native of Asia, the soybean aphid (*Aphis glycines* Matsumura) was first found in the Midwest in 2000 (Hartman, G. L., et al., "Occurrence and distribution of *Aphis glycines* on soybeans in Illinois in 2000 and its potential control," (1 Feb. 2001) Plant Management Network website). It rapidly spread throughout the region and into other parts of North America (Patterson, J. and Ragsdale, D., "Assessing and managing risk from soybean aphids in the North Central States," (11 Apr. 2002) Soybean Research and Information Initiative website). High aphid populations can reduce crop production directly when their feeding causes severe damage such as stunting, leaf distortion, and reduced pod set (Sun, Z., et al., "Study on the uses of aphid-resistant character in wild soybean. I. Aphid-resistance performance of F2 generation from crosses between cultivated and wild soybeans," (1990) Soybean Genet. News. 17:43-48). Yield losses attributed to the aphid in some fields in Minnesota during 2001, where several thousand aphids occurred on individual soybean plants, were >50% (Ostlie, K., "Managing soybean aphid," (2 Oct. 2002) University of Minnesota website), with an average loss of 101 to 202 kg/ha in those fields (Patterson, J. and Ragsdale, D., "Assessing and managing risk from soybean aphids in the North Central States," (11 Apr. 2002). In earlier reports from China, soybean yields were reduced up to 52% when there was an average of about 220 aphids per plant (Wang, X. B., et al., "A study on the damage and economic threshold of the soybean aphid at the seedling stage," (1994) Plant Prot. (China) 20:12-13), and plant height was decreased by about 210 mm after severe aphid infestation (Wang, X. B., et al., "Study on the effects of the population dynamics of soybean aphid (*Aphis glycines*) on both growth and yield of soybean," (1996) Soybean Sci. 15:243-247). An additional threat posed by the aphid is its ability to transmit certain plant viruses to soybean, such as Alfalfa mosaic virus, Soybean dwarf virus, and Soybean mosaic virus (Sama, S., et al., "Varietal screening for resistance to the aphid, *Aphis glycines*, in soybean," (1974) Research Reports 1968-1974, pp. 171-172; Iwaki, M., et al., "A persistent aphid borne virus of soybean, Indonesian Soybean dwarf virus transmitted by *Aphis glycines*," (1980) Plant Dis. 64:1027-1030; Hartman, G. L., et al., "Occurrence and distribution of *Aphis glycines* on soybeans in Illinois in 2000 and its potential control," (1 Feb. 2001) Plant Management Network website; Hill, J. H., et al., "First report of transmission of Soybean mosaic virus and Alfalfa mosaic virus by *Aphis glycines* (Homoptera, Aphididae)," (1996) Appl. Entomol. 2001. 31:178-180; Clark, A. J. and Perry, K. L., "Transmissibility of field isolates of soybean viruses by *Aphis glycines*," (2002) Plant Dis. 86:1219-1222).

Currently, millions of dollars are spent annually on spraying insecticides to control soybean aphid infestation. An integral component of an integrated pest management (IPM) program to control aphids is plant resistance (Auclair, J. L., "Host plant resistance," pp. 225-265 In P. Harrewijn (ed.) Aphids: Their biology, natural enemies, and control, Vol. C., Elsevier, New York (1989); Harrewijn, P. and Minks, A. K., "Integrated aphid management: General aspects," pp. 267-272, In A. K. Minks and P. Harrewijn (ed.) Aphids: Their biology, natural enemies, and control, Vol. C., Elsevier, New York (1989)). Insect resistance can significantly reduce input costs for producers (Luginbill, J. P., "Developing resistant plants—The ideal method of controlling insects," (1969) USDA, ARS. Prod. Res. Rep. 111, USGPO, Washington, D.C.).

There are currently three well-documented biotypes (i.e., a subspecies of soybean aphid that shares certain genetic traits or a specified genotype) of soybean aphid that have been collected in Urbana, Ill. (biotype 1), Wooster, Ohio (biotype 2), and Indiana (biotype 3). Additionally, there are three kinds of plant resistance that have been identified: antibiosis, antixenosis, and tolerance. Antibiosis (non-choice) is the plant's ability to reduce the survival, reproduction, and fecundity of the insect. Antixenosis (choice) is the plant's ability to deter the insect from feeding or identifying the plant as a food source. Tolerance is the plant's ability to withstand heavy infestation without significant yield loss.

To date, three different soybean aphid resistance genes have been identified and mapped to the soybean genome. Rag1 was the first soybean resistance gene identified (Mian, et al., Genetic linkage mapping of the soybean aphid resistance gene in PI 243540, Theor. Appl. Genet. 117:955-962 (2008)). Rag1 has been mapped to linkage group M in the vicinity of SSR markers Satt540 and Satt463 (Kim, et al., Fine mapping of the soybean aphid resistance gene Rag1 in soybean, Theor. Appl. Genet., 120:1063-1071 (2010)). Rag2 has been mapped to linkage group F in the vicinity of SSR markers Satt334 and Sct_033 (Mian, et al., Genetic linkage mapping of the soybean aphid resistance gene in PI 243540, Theor. Appl. Genet. 117:955-962 (2008)). Rag3 is located on linkage group J in the vicinity of markers Sat_339 and Sat_370. It has also been previously determined that some aphid biotypes are resistant to certain of the Rag genes but are susceptible to others (Mian, et al., Genetic linkage mapping of the soybean aphid resistance gene in PI 243540, Theor. Appl. Genet. 117:955-962 (2008)).

Molecular markers have been used to selectively improve soybean crops through the use of marker assisted selection. Any detectible polymorphic trait can be used as a marker so long as it is inherited differentially and exhibits linkage disequilibrium with a phenotypic trait of interest. A number of soybean markers have been mapped and linkage groups created, as described in Cregan, R B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website (Soybase and the Soybean Breeder's Toolbox website).

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

In some cases, multiple closely linked markers, such as Single Nucleotide Polymorphism (SNP) markers, can be found to exist in a certain region of a plant genome encompassing one or more QTL. In such cases, by determining the allele present at each of those marker loci, a haplotype for that region of the plant genome can be determined. Further, by determining alleles or haplotypes present at multiple regions of the plant genome related to the same phenotypic trait, a marker profile for that trait can be determined. Such haplotype and marker profile information can be useful in identifying and selecting plants with certain desired traits.

There remains a need for soybean plants with improved resistance to soybean aphid and methods for identifying and selecting such plants.

SUMMARY

This invention relates to methods of improving resistance to aphids in soybean plants, as well as methods for identifying and/or selecting soybean plants or germplasm that display improved resistance to one or more biotypes of soybean aphid. In certain examples, the method comprises selecting a first and second soybean plant or germplasm, each of which has a different favorable Rag1, Rag2, or Rag3, allele, haplotype, or marker profile, and crossing those first and second soybean plants to produce a progeny plant with stacked Rag alleles, haplotypes, or marker profiles and improved soybean aphid resistance. In other examples, the method comprises detecting a stacked marker profile comprising two or more Rag haplotypes. This invention further relates to markers, primers, probes, kits, systems, etc., useful for carrying out the methods described herein.

BRIEF DESCRIPTION OF THE FIGURES

FIGS. 1A-1C illustrate a partial genetic map of soybean illustrating the relative map position of the Rag intervals and numerous linked marker loci. FIG. 1A illustrates a genetic map of linkage group M and the relative map position of the Rag1 interval. FIG. 1B illustrates a genetic map of linkage group F and the relative map position of the Rag2 interval. FIG. 1C illustrates a genetic map of linkage group J and the relative map position of the Rag3 interval.

SUMMARY OF THE SEQUENCES

SEQ ID NOs: 1-4 comprise nucleotide sequences of regions of the soybean genome, each capable of being used as a probe or primer, either alone or in combination, for the detection of marker locus S14181-1-Q1 on LG-M. In certain examples, SEQ ID NOs: 1 and 2 are used as primers while SEQ ID NOs: 3 and 4 are used as probes.

SEQ ID NO: 5 is the genomic DNA region encompassing marker locus S14181-1-Q1 on LG-M. In certain examples this sequence is used to design primers and probes directed toward this marker. In certain other examples this sequence, or a portion of it, is used as a probe to detect this marker.

SEQ ID NOs: 6-9 comprise nucleotide sequences of regions of the soybean genome, each capable of being used as a probe or primer, either alone or in combination, for the detection of marker locus S13871-1-Q1 on LG-M. In certain examples, SEQ ID NOs: 6 and 7 are used as primers while SEQ ID NOs: 8 and 9 are used as probes.

SEQ ID NO: 10 is the genomic DNA region encompassing marker locus S13871-1-Q1 on LG-M. In certain examples this sequence is used to design primers and probes directed toward this marker. In certain other examples this sequence, or a portion of it, is used as a probe to detect this marker.

SEQ ID NOs: 11-14 comprise nucleotide sequences of regions of the soybean genome, each capable of being used as a probe or primer, either alone or in combination, for the detection of marker locus S14161-1-Q10 on LG-M. In certain examples, SEQ ID NOs: 11 and 12 are used as primers while SEQ ID NOs: 13 and 14 are used as probes.

SEQ ID NO: 15 is the genomic DNA region encompassing marker locus S14161-1-Q10 on LG-M. In certain examples this sequence is used to design primers and probes directed toward this marker. In certain other examples this sequence, or a portion of it, is used as a probe to detect this marker.

SEQ ID NOs: 16-19 comprise nucleotide sequences of regions of the soybean genome, each capable of being used as a probe or primer, either alone or in combination, for the detection of marker locus S09515-1-Q1 on LG-M. In certain examples, SEQ ID NOs: 16 and 17 are used as primers while SEQ ID NOs: 18 and 19 are used as probes.

SEQ ID NO: 20 is the genomic DNA region encompassing marker locus S09515-1-Q1 on LG-M. In certain examples this sequence is used to design primers and probes directed toward this marker. In certain other examples this sequence, or a portion of it, is used as a probe to detect this marker.

SEQ ID NOs: 21-24 comprise nucleotide sequences of regions of the soybean genome, each capable of being used as a probe or primer, either alone or in combination, for the detection of marker locus S14151-1-Q1 on LG-M. In certain examples, SEQ ID NOs: 21 and 22 are used as primers while SEQ ID NOs: 23 and 24 are used as probes.

SEQ ID NO: 25 is the genomic DNA region encompassing marker locus S14151-1-Q1 on LG-M. In certain examples this sequence is used to design primers and probes directed toward this marker. In certain other examples this sequence, or a portion of it, is used as a probe to detect this marker.

SEQ ID NOs: 26-29 comprise nucleotide sequences of regions of the soybean genome, each capable of being used as a probe or primer, either alone or in combination, for the detection of marker locus S14151-2-Q4 on LG-M. In certain examples, SEQ ID NOs: 26 and 27 are used as primers while SEQ ID NOs: 28 and 29 are used as probes.

SEQ ID NO: 30 is the genomic DNA region encompassing marker locus S14151-2-Q4 on LG-M. In certain examples this sequence is used to design primers and probes directed toward this marker. In certain other examples this sequence, or a portion of it, is used as a probe to detect this marker.

SEQ ID NOs: 31-34 comprise nucleotide sequences of regions of the soybean genome, each capable of being used as a probe or primer, either alone or in combination, for the detection of marker locus S07164-1-Q12 on LG-M. In certain examples, SEQ ID NOs: 31 and 32 are used as primers while SEQ ID NOs: 33 and 34 are used as probes.

SEQ ID NO: 35 is the genomic DNA region encompassing marker locus S07164-1-Q12 on LG-M. In certain examples this sequence is used to design primers and probes directed toward this marker. In certain other examples this sequence, or a portion of it, is used as a probe to detect this marker.

SEQ ID NOs: 36-39 comprise nucleotide sequences of regions of the soybean genome, each capable of being used as a probe or primer, either alone or in combination, for the detection of marker locus S14182-1-Q1 on LG-M. In certain examples, SEQ ID NOs: 36 and 37 are used as primers while SEQ ID NOs: 38 and 39 are used as probes.

SEQ ID NO: 40 is the genomic DNA region encompassing marker locus S14182-1-Q1 on LG-M. In certain examples this sequence is used to design primers and probes directed toward this marker. In certain other examples this sequence, or a portion of it, is used as a probe to detect this marker.

SEQ ID NOs: 41-44 comprise nucleotide sequences of regions of the soybean genome, each capable of being used as a probe or primer, either alone or in combination, for the detection of marker locus S00812-1-A on LG-M. In certain examples, SEQ ID NOs: 41 and 42 are used as primers while SEQ ID NOs: 43 and 44 are used as probes.

SEQ ID NO: 45 is the genomic DNA region encompassing marker locus S00812-1-A on LG-M. In certain examples this sequence is used to design primers and probes directed toward this marker. In certain other examples this sequence, or a portion of it, is used as a probe to detect this marker.

SEQ ID NOs: 46-49 comprise nucleotide sequences of regions of the soybean genome, each capable of being used as a probe or primer, either alone or in combination, for the detection of marker locus S02780-1-A on LG-M. In certain examples, SEQ ID NOs: 46 and 47 are used as primers while SEQ ID NOs: 48 and 49 are used as probes.

SEQ ID NO: 50 is the genomic DNA region encompassing marker locus S02780-1-A on LG-M. In certain examples this sequence is used to design primers and probes directed toward this marker. In certain other examples this sequence, or a portion of it, is used as a probe to detect this marker.

SEQ ID NOs: 51-54 comprise nucleotide sequences of regions of the soybean genome, each capable of being used as a probe or primer, either alone or in combination, for the detection of marker locus S14761-001-Q001 on LG-F. In certain examples, SEQ ID NOs: 51 and 52 are used as primers while SEQ ID NOs: 53 and 54 are used as probes.

SEQ ID NO: 55 is the genomic DNA region encompassing marker locus S14761-001-Q001 on LG-F. In certain examples this sequence is used to design primers and probes directed toward this marker. In certain other examples this sequence, or a portion of it, is used as a probe to detect this marker.

SEQ ID NOs: 56-59 comprise nucleotide sequences of regions of the soybean genome, each capable of being used as a probe or primer, either alone or in combination, for the detection of marker locus S14771-001-Q001 on LG-F. In certain examples, SEQ ID NOs: 56 and 57 are used as primers while SEQ ID NOs: 58 and 59 are used as probes.

SEQ ID NO: 60 is the genomic DNA region encompassing marker locus S14771-001-Q001 on LG-F. In certain examples this sequence is used to design primers and probes directed toward this marker. In certain other examples this sequence, or a portion of it, is used as a probe to detect this marker.

SEQ ID NOs: 61-64 comprise nucleotide sequences of regions of the soybean genome, each capable of being used as a probe or primer, either alone or in combination, for the detection of marker locus S07165-1-Q3 on LG-F. In certain examples, SEQ ID NOs: 61 and 62 are used as primers while SEQ ID NOs: 63 and 64 are used as probes.

SEQ ID NO: 65 is the genomic DNA region encompassing marker locus S07165-1-Q3 on LG-F. In certain examples this sequence is used to design primers and probes directed toward this marker. In certain other examples this sequence, or a portion of it, is used as a probe to detect this marker.

SEQ ID NOs: 66-69 comprise nucleotide sequences of regions of the soybean genome, each capable of being used as a probe or primer, either alone or in combination, for the detection of marker locus S14778-001-Q001 on LG-F. In certain examples, SEQ ID NOs: 66 and 67 are used as primers while SEQ ID NOs: 68 and 69 are used as probes.

SEQ ID NO: 70 is the genomic DNA region encompassing marker locus S14778-001-Q001 on LG-F. In certain examples this sequence is used to design primers and probes directed toward this marker. In certain other examples this sequence, or a portion of it, is used as a probe to detect this marker.

SEQ ID NOs: 71-74 comprise nucleotide sequences of regions of the soybean genome, each capable of being used as a probe or primer, either alone or in combination, for the detection of marker locus S01164-1-Q1 on LG-F. In certain examples, SEQ ID NOs: 71 and 72 are used as primers while SEQ ID NOs: 73 and 74 are used as probes.

SEQ ID NO: 75 is the genomic DNA region encompassing marker locus S01164-1-Q1 on LG-F. In certain examples this sequence is used to design primers and probes directed toward this marker. In certain other examples this sequence, or a portion of it, is used as a probe to detect this marker.

SEQ ID NOs: 76-83 comprise nucleotide sequences of regions of the soybean genome, each capable of being used as a probe or primer, either alone or in combination, for the detection of marker locus S13662-1-Q3/Q6 on LG-J. In certain examples, SEQ ID NOs: 76 and 77 are used as primers while SEQ ID NOs: 78 and 79 are used as probes to amplify and detect S13662-1-Q3. In other examples, SEQ ID NOs: 80 and 81 are used as primers while SEQ ID NOs: 82 and 83 are used as probes to amplify and detect S13662-1-Q6.

SEQ ID NO: 84 is the genomic DNA region encompassing marker locus S13662-1-Q3/Q6 on LG-J. In certain examples this sequence is used to design primers and probes directed toward this marker. In certain other examples this sequence, or a portion of it, is used as a probe to detect this marker.

SEQ ID NOs: 85-88 comprise nucleotide sequences of regions of the soybean genome, each capable of being used as a probe or primer, either alone or in combination, for the detection of marker locus S13663-1-Q1 on LG-J. In certain examples, SEQ ID NOs: 85 and 86 are used as primers while SEQ ID NOs: 87 and 88 are used as probes.

SEQ ID NO: 89 is the genomic DNA region encompassing marker locus S13663-1-Q1 on LG-J. In certain examples this sequence is used to design primers and probes directed toward this marker. In certain other examples this sequence, or a portion of it, is used as a probe to detect this marker.

SEQ ID NOs: 90-93 comprise nucleotide sequences of regions of the soybean genome, each capable of being used as a probe or primer, either alone or in combination, for the detection of marker locus S11411-1-Q1 on LG-J. In certain examples, SEQ ID NOs: 90 and 91 are used as primers while SEQ ID NOs: 92 and 93 are used as probes.

SEQ ID NO: 94 is the genomic DNA region encompassing marker locus S11411-1-Q1 on LG-J. In certain examples this sequence is used to design primers and probes directed toward this marker. In certain other examples this sequence, or a portion of it, is used as a probe to detect this marker.

SEQ ID NOs: 95-102 comprise nucleotide sequences of regions of the soybean genome, each capable of being used as a probe or primer, either alone or in combination, for the detection of marker locus S13664-1-Q1/Q002 on LG-J. In certain examples, SEQ ID NOs: 95 and 96 are used as primers while SEQ ID NOs: 97 and 98 are used as probes to amplify and detect S13664-1-Q1. In other examples, SEQ ID NOs: 99 and 100 are used as primers while SEQ ID NOs: 101 and 102 are used as probes to amplify and detect S13664-1-Q002.

SEQ ID NO: 103 is the genomic DNA region encompassing marker locus S13664-1-Q002 on LG-J. In certain examples this sequence is used to design primers and probes directed toward this marker. In certain other examples this sequence, or a portion of it, is used as a probe to detect this marker.

SEQ ID NOs: 104-113 comprise nucleotide sequences of regions of the soybean genome, each capable of being used as a probe or primer, either alone or in combination, for the detection of marker locus S13672-1-Q1/Q2/Q3 on LG-J. In certain examples, SEQ ID NOs: 104 and 105 are used as primers while SEQ ID NOs: 106 and 107 are used as probes to amplify and detect S13672-1-Q1. In other examples, SEQ ID NOs: 108 and 109 are used as primers while SEQ ID NOs: 106 and 107 are used as probes to amplify and detect S13672-1-Q2. In still further examples, SEQ ID NOs: 110 and 111 are used as primers while SEQ ID NOs: 112 and 113 are used as probes to amplify and detect S13672-1-Q3.

SEQ ID NO: 114 is the genomic DNA region encompassing marker locus S13672-1-Q1/Q2/Q3 on LG-J. In certain examples this sequence is used to design primers and probes directed toward this marker. In certain other examples this sequence, or a portion of it, is used as a probe to detect this marker.

SEQ ID NOs: 115-120 comprise nucleotide sequences of regions of the soybean genome, each capable of being used as a probe or primer, either alone or in combination, for the detection of marker locus S13674-1-Q1/Q007 on LG-J. In certain examples, SEQ ID NOs: 115 and 116 are used as primers while SEQ ID NOs: 117 and 118 are used as probes to amplify and detect S13674-1-Q1. In other examples, SEQ ID NOs: 119 and 120 are used as primers while SEQ ID NOs: 117 and 118 are used as probes to amplify and detect S13674-1-Q007.

SEQ ID NO: 121 is the genomic DNA region encompassing marker locus S13674-1-Q1/Q007 on LG-J. In certain examples this sequence is used to design primers and probes directed toward this marker. In certain other examples this sequence, or a portion of it, is used as a probe to detect this marker.

SEQ ID NOs: 122-125 comprise nucleotide sequences of regions of the soybean genome, each capable of being used as a probe or primer, either alone or in combination, for the detection of marker locus S13675-2-Q1 on LG-J. In certain examples, SEQ ID NOs: 122 and 123 are used as primers while SEQ ID NOs: 124 and 125 are used as probes.

SEQ ID NO: 126 is the genomic DNA region encompassing marker locus S13675-2-Q1 on LG-J. In certain examples this sequence is used to design primers and probes directed toward this marker. In certain other examples this sequence, or a portion of it, is used as a probe to detect this marker.

SEQ ID NOs: 127-130 comprise nucleotide sequences of regions of the soybean genome, each capable of being used as a probe or primer, either alone or in combination, for the detection of marker locus S01190-1-A on LG-F. In certain examples, SEQ ID NOs: 127 and 128 are used as primers while SEQ ID NOs: 129 and 130 are used as probes.

SEQ ID NO: 131 is the genomic DNA region encompassing marker locus S01190-1-A on LG-F. In certain examples this sequence is used to design primers and probes directed toward this marker. In certain other examples this sequence, or a portion of it, is used as a probe to detect this marker.

SEQ ID NOs: 132-135 comprise nucleotide sequences of regions of the soybean genome, each capable of being used as a probe or primer, either alone or in combination, for the detection of marker locus S25354-001-Q001 on LG-M. In certain examples, SEQ ID NOs: 132 and 133 are used as primers while SEQ ID NOs: 134 and 135 are used as probes.

SEQ ID NO: 136 is the genomic DNA region encompassing marker locus S15354-001-Q001 on LG-M. In certain examples this sequence is used to design primers and probes directed toward this marker. In certain other examples this sequence, or a portion of it, is used as a probe to detect this marker.

DETAILED DESCRIPTION

In one embodiment, a novel method is provided for improving resistance to one or more soybean aphid biotypes in a soybean germplasm, plant, line, or strain, the method comprising a) selecting a first soybean plant or germplasm, or a progeny thereof, wherein said first soybean plant, germplasm, or progeny comprises a favorable allele, haplotype, or marker profile of at least one of Rag1, Rag2, and Rag3; and selecting a second soybean plant or germplasm, or a progeny thereof, wherein said second soybean plant, germplasm, or progeny comprises a favorable allele, haplotype, or marker profile of at least one of Rag1, Rag2, and Rag3 different than that of said first soybean plant, germplasm, or progeny; and b) crossing the first soybean plant, germplasm, or progeny with the second soybean plant, germplasm, or progeny to produce a progeny plant with stacked Rag alleles, haplotypes, or marker profiles and improved soybean aphid resistance.

In some examples, the Rag1 haplotype comprises one or more markers that fall within the interval flanked by and including Satt435 and Sat_244, the Rag2 haplotype comprises one or more markers that fall within the interval flanked by and including Satt334 and Satt510, and/or the Rag3 haplotype comprises one or more markers that fall within the interval flanked by and including Sat_339 and Sat_370. In other examples, the Rag1 haplotype comprises one or more markers that fall within the interval flanked by and including physical position 5464314-8194502 on LG-M on the Glyma1 soybean genome assembly (see, e.g., Schmutz J, et al. (2010). "Genome sequence of the palaeopolyploid soybean." *Nature* 463, 178-183; see also, Phytozome website; each of which is incorporated herein by reference in its entirety), the Rag2 haplotype comprises one or more markers that fall within the interval flanked by and including physical position 28416122-30590233 on LG-F on the Glyma1 soybean genome assembly, and/or the Rag3 haplotype comprises one or more markers that fall within the interval flanked by and including physical position 4157916-7054678 on LG-J on the Glyma1 soybean genome assembly.

In further examples, the at least one Rag haplotype comprises marker loci selected from the group consisting of: (a) one or more marker loci selected from the group consisting of S15354-001-Q001, S1418'-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A; (b) one or more marker loci selected from the group consisting of S01190-1-A, S14761-001-Q001, S14771-001-Q001, S07165-1-Q3, S14778-001-Q001, and S01164-1-Q1; and (c) one or more marker loci selected from the group consisting of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In still further examples, the at least one Rag haplotype comprises two or more of the marker loci within one or more of (a), (b), or (c). In other examples, the at least one Rag haplotype comprises three or more of the marker loci within one or more of (a), (b), or (c). In yet other examples, the at least one Rag haplotype comprises four or more of the marker loci within one or more of (a), (b), or (c). In even further examples, the at least one Rag haplotype comprises all of the marker loci within one or more of (a), (b), or (c).

In certain examples the first soybean plant, germplasm, or progeny and said second soybean plant, germplasm, or progeny collectively comprise a favorable allele, haplotype, or marker profile of all three of Rag1, Rag2, and Rag3.

In other examples, the improved soybean aphid resistance comprises either improved antibiosis resistance or improved antixenosis resistance. In yet other examples, the improved soybean aphid resistance comprises both improved antibiosis resistance and improved antixenosis resistance. In additional examples, the improved soybean aphid resistance comprises improved resistance to at least two soybean aphid biotypes, at least three soybean aphid phenotypes, at least four soybean aphid phenotypes, or at least five soybean aphid biotypes.

In additional examples, the method further comprises detecting the favorable Rag allele, the detecting step comprising amplifying a marker nucleic acid or a portion of the marker nucleic acid. In other examples, the method further comprises detecting the resulting amplified marker nucleic acid. In certain particular examples, the amplifying comprises performing a polymerase chain reaction (PCR) using one or more nucleic acids from the plant as a template in the PCR.

In some particular examples, the method comprises amplifying at least a portion of one or more genome regions selected from the group consisting of SEQ ID NOs: 5, 10, 15, 20, 25, 30, 35, 40, 45, 50, 55, 60, 65, 70, 75, 84, 89, 94, 103, 114, 121, 126, 131, and 136. In other examples, the primer or primer pair comprises a nucleic acid sequence selected from the group consisting of SEQ ID NOs: 1, 2, 6, 7, 11, 12, 16, 17, 21, 22, 26, 27, 31, 32, 36, 37, 41, 42, 46, 47, 51, 52, 56, 57, 61, 62, 66, 67, 71, 72, 76, 77, 80, 81, 85, 86, 90, 91, 95, 96, 99, 100, 104, 105, 108, 109, 110, 111, 115, 116, 119, 120, 122, 123, 127, 128, 132, and 133.

In certain other examples, the detecting further comprises providing a detectable probe. In some particular examples, the probe comprises a nucleic acid sequence selected from the group consisting of SEQ ID NOs: 3, 4, 8, 9, 13, 14, 18, 19, 23, 24, 28, 29, 33, 34, 38, 39, 43, 44, 48, 49, 53, 54, 58, 59, 63, 64, 68, 69, 73, 74, 78, 79, 82, 83, 87, 88, 92, 93, 97, 98, 101, 102, 106, 107, 112, 113, 117, 118, 124, 125, 129, 130, 134, and 135. In other examples, the probe comprises at least a portion of a nucleic acid sequence selected from the group consisting of SEQ ID NOs: 5, 10, 15, 20, 25, 30, 35 40, 45, 50, 55, 60, 65, 70, 75, 84, 89, 94, 103, 114, 121, 126, 131, and 136.

In further embodiments, the invention relates to a method of selecting a soybean plant or germplasm that displays improved resistance to one or more soybean aphid biotypes. In certain examples, the improved resistance comprises one or more of improved antibiosis resistance or improved antixenosis resistance. In other examples, the improved resistance comprises both improved antibiosis and antixenosis resistance. In further examples, the improved soybean aphid resistance comprises improved resistance to at least two soybean aphid biotypes. In other examples, the improved soybean aphid resistance comprises improved resistance to at least three soybean aphid biotypes. In still further examples, the improved soybean aphid resistance comprises improved resistance to at least four soybean aphid biotypes or at least five soybean aphid biotypes.

In certain examples, the method comprises detecting in a first soybean plant or germplasm, or a part thereof, a favorable allele of at least two of Rag1, Rag2, and Rag3; and selecting the first soybean plant or germplasm, or selecting a progeny of the first soybean plant or germplasm. In additional examples, the detecting involves detection of a favorable allele of all three of Rag1, Rag2, and Rag3.

In certain particular examples, the detecting comprises amplifying a marker nucleic acid or a portion of the marker nucleic acid and detecting the resulting amplified marker nucleic acid. In additional examples, the amplifying comprises performing a polymerase chain reaction (PCR) using one or more nucleic acid from the plant as a template in the PCR.

In yet further examples, the method further comprises crossing the selected first soybean plant or germplasm with a second soybean plant or germplasm. In particular examples, the second soybean plant or germplasm comprises an exotic soybean strain or an elite soybean strain.

Plants, including soybean plants, seeds, tissue cultures, variants and mutants, having improved soybean aphid resistance are also provided. In certain examples, plants produced by the foregoing methods are provided. In other examples, elite lines having a stacked Rag haplotype are provided. In additional examples, plants comprising a stack comprising one or more the Rag haplotypes or marker profiles discussed herein are provided. In yet further examples, plants comprising a stack comprising one or more favorable or disfavored alleles at the marker loci discussed herein are provided. In certain examples, plants comprising stack comprising one or more Rag haplotype selected from the group consisting of Rag1-b, Rag1-c, Rag2-d, Rag3-b, and Rag3-d are provided. In certain other examples, plants comprising a stack comprising a haplotype or marker profile selected from the group consisting of (a) Rag1-b/Rag3-b; (b) Rag1-b; (c) Rag1-c/Rag3-d; (d) Rag1-e; and (e) Rag1-d/Rag2-c are provided. In some specific examples, plants are provided that have a Rag-1/Rag-2 stack and that possess improved resistance to aphid biotype 3. In yet further examples, plants comprising a stack comprising one or more favorable or disfavored allele at (a) one or more marker loci selected from the group consisting S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A; (b) one or more marker loci selected from the group consisting of S01190-1-A, S14761-001-Q001, S14771-001-Q001, S07165-1-Q3, S14778-001-Q001, and S01164-1-Q1; or (c) one or more marker loci selected from the group consisting of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1 are provided. In further examples, plants comprising a stack comprising one or more favorable or disfavored allele at (a) the marker loci S14161-1-Q10, S09515-1-Q1, S14151-2-Q4, and S07164-1-Q12; (b) the marker loci S07165-1-Q3, S01190-1-A, and S01164-1-Q1; or (c) the marker loci S11411-1-Q1, S13674-1-Q1/Q007, and S13675-2-Q1 are provided.

Also provided are isolated nucleic acids, kits, and systems useful for the identification and selection methods disclosed herein. In certain examples, isolated nucleic acids, kits, and systems useful for the detection of the Rag haplotypes or marker profiles discussed herein are provided. In yet further examples, isolated nucleic acids, kits, and systems useful for the detection of the favorable or disfavored alleles at the marker loci discussed herein are provided. In certain examples, isolated nucleic acids, kits, and systems useful for the detection of a Rag haplotype selected from the group consisting of Rag1-b, Rag1-c, Rag2-d, Rag3-b, and Rag3-d are provided. In certain other examples, isolated nucleic acids, kits, and systems useful for the detection of a haplotype or marker profile selected from the group consisting of (a) Rag1-b/Rag3-b; (b) Rag1-b; (c) Rag1-c/Rag3-d; (d) Rag1-e; and (e) Rag1-d/Rag2-c are provided. In yet further examples, isolated nucleic acids, kits, and systems useful for the detection of a favorable or disfavored allele at (a) one or more marker loci selected from the group consisting S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A; (b) one or more marker loci selected from the group consisting of S01190-1-A, S14761-001-Q001, S14771-001-Q001, S07165-1-Q3, S14778-001-Q001, and S01164-1-Q1; or (c) one or more marker loci selected from the group consisting of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1 are provided. In further examples, isolated nucleic acids, kits, and systems useful for the detection of a favorable or disfavored allele at (a) the marker loci S14161-1-Q10, S09515-1-Q1, S14151-2-Q4, and S07164-1-Q12; (b) the marker loci S07165-1-Q3, S01190-1-A, and S01164-1-Q1; or (c) the marker loci S11411-1-Q1, S13674-1-Q1/Q007, and S13675-2-Q1 are provided.

It is to be understood that this invention is not limited to particular embodiments, which can, of course, vary. It is also to be understood that the terminology used herein is for the purpose of describing particular embodiments only, and is not intended to be limiting. Further, all publications referred to herein are incorporated by reference herein for the purpose cited to the same extent as if each was specifically and individually indicated to be incorporated by reference herein.

DEFINITIONS

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

"Biotype" or "aphid biotype" means a subspecies of soybean aphid that share certain genetic traits or a specified genotype. There are currently three well-documented biotypes of soybean aphid: Urbana, Ill. (biotype 1), Wooster, Ohio (biotype 2), and Indiana (biotype 3). An additional biotype, referred to herein as biotype X, was collected from soybean fields in Lime Springs, Iowa. A further biotype, referred to herein as biotype Y, was collected from a field near Lomira, Wis. in summer 2011.

The term "chromosome segment" designates a contiguous linear span of genomic DNA that resides in planta on a single chromosome.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, haplotype, marker profile, trait, or trait locus from the genome of one plant into the genome of another plant.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A $\frac{1}{100}$ probability of recombination per generation is defined as a map distance of 1.0 centiMorgan (1.0 cM).

The genetic elements or genes located on a single chromosome segment are physically linked. Advantageously, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers. As such, a linkage group can generally be assigned to a certain chromosome, and such associations are well known in the art, for example from the soybase database (Soybase and the Soybean Breeder's Toolbox website). For example, soybean LG-M corresponds to soybean chromosome 7, soybean LG-F corresponds to soybean chromosome 13, and soybean LG-J corresponds to soybean chromosome 16.

"Locus" is a defined segment of DNA.

A "map location" is an assigned location on a genetic map relative to linked genetic markers where a specified marker can be found within a given species.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known in the art, and phenotypic traits may also be used as markers in the methods. All markers are used to define a specific locus on the soybean genome. Large numbers of these markers have been mapped (see, e.g., Soybase and the Soybean Breeder's Toolbox website). Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage where the trait can be expressed. Molecular markers have been widely used to determine genetic composition in soybeans.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or Taq-Man™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

"PRMMAT" means Predicted Relative Maturity. Soybean maturities are divided into relative maturity groups. In the United States the most common maturity groups are 00 through VIII. Within maturity groups 00 through V are sub-groups. A sub-group is a tenth of a relative maturity group. Within narrow comparisons, the difference of a tenth of a relative maturity group equates very roughly to a day difference in maturity at harvest.

"Rag genes," "Rag intervals," "Rag QTL," and "Rag loci" refer to one or more of the Rag1, Rag2, and Rag3 genes and the chromosome segments or intervals on which they are located. Rag1 maps to linkage group M. In some examples, the Rag1 interval is defined as being flanked by and including markers Satt540 and BARC-016783-02329. In other examples, the Rag1 interval is defined as being flanked by and including markers BARC-039195-07466 and BARC-016783-02329. Rag2 maps to linkage group F. In some examples, the Rag2 interval is defined as being flanked by and including markers Satt334 and Sat_317. In other examples, the Rag2 interval is defined as being flanked by and including markers BARC-029823-06424 and Sct_033. Rag3 maps to linkage group J. In some examples, the Rag 3 interval is defined as being flanked by and including markers Sat_339 and Sct_065. In other examples, the Rag3 interval is defined as being flanked by and including markers BARC-031195-07010 and Sat_370.

"Rag haplotype" or simply "haplotype" means the combination of particular alleles present within a particular plant's genome at one or more specific marker loci within or linked to the Rag1, Rag2, or Rag3 interval or gene. For instance, in one example, one specific SNP locus within or linked to the Rag1 interval is used to define a Rag1 haplotype for a particular plant. In another example, two specific SNP loci within or linked to the Rag1 interval are used to define a Rag1 haplotype for a particular plant. In still further examples, 3, 4, 5, 6, 7, 8, 9, 10, 11, 12, 13, 14, 15, 16, 17, 18, 19, 20, or more specific SNP loci within or linked to the Rag1 interval are used to define a Rag1 haplotype for a particular plant. The same applies for the Rag2 and Rag3 intervals.

In certain examples, multiple Rag haplotypes are used to define a "marker profile" or "Rag marker profile." As used herein, "marker profile" means the combination of two or more Rag haplotypes within a particular plant's genome. For instance, in one example, a particular Rag1 haplotype and a particular Rag2 haplotype define the marker profile of a particular plant. In another example, a particular Rag1 haplotype and a particular Rag3 haplotype define the marker profile of a particular plant. In a still further example, a particular Rag2 haplotype and a particular Rag3 haplotype define the marker profile of a particular plant. In an additional example, a particular Rag1 haplotype, a particular Rag2 haplotype, and a particular Rag3 haplotype define the marker profile of a particular plant. More specifically, a particular plant marker profile might be, for example, Rag1-a/Rag2-a or Rag1-b/Rag2-a/Rag3-c.

"Recombination frequency" is the frequency of a crossing over event (recombination) between two genetic loci. Recombination frequency can be observed by following the segregation of markers and/or traits during meiosis.

"Resistance" and "improved resistance" are used interchangeably herein and refer to one or more of antibiosis resistance, antixenosis resistance, and tolerance to soybean aphid. "Antibiosis" refers to the plant's ability to reduce the survival, reproduction, and fecundity of the insect. "Antixenosis" refers to the plant's ability to deter the insect from feeding or identifying the plant as a food source. "Tolerance" refers to the plant's ability to withstand heavy infestation without significant yield loss. A "resistant plant" or "resistant plant variety" need not possess absolute or complete resistance to one or more soybean aphid biotypes. Instead, a "resistant plant," "resistant plant variety," or a plant or plant variety with "improved resistance" will have a level of resistance to at least one soybean aphid biotype which is higher than that of a comparable susceptible plant or variety.

"Self crossing," "self pollination," or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome. Many techniques for detecting SNPs are known in the art, including allele specific hybridization, primer extension, direct sequencing, and real-time PCR, such as the TaqMan™ assay.

"Stacking" refers to a process of producing a plant that has two or more particular alleles, haplotypes, or traits (generally desirable) that were received from different sources. For instance a plant with "stacked" alleles, may be produced by breeding two parental plants, each of which has a different desirable allele, haplotype, or trait. The stacked alleles, haplotypes, or traits may relate to the same phenotype, for instance alleles for different markers that both relate to aphid resistance, or may relate to different phenotypic traits, for instance stacking a favorable aphid resistance allele with a favorable drought resistance allele. Additionally, stacking can involve two or more alleles/haplotypes at the same locus (e.g., Rag1a/Rag1b), or different alleles/haplotypes at two or more distinct loci (e.g., Rag1a/Rag1b, Rag2a/Rag2b). Stacking can be done by any suitable method, including through transgenic approaches or through breeding. In some instances, stacking is performed by using marker-assisted selection to select parental plants with two or more desired alleles, haplotypes, or traits and then crossing those plants to produce a stacked progeny plant.

"Transgenic plant" refers to a plant that comprises within its cells an exogenous polynucleotide. Generally, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to refer to any cell, cell line, callus, tissue, plant part, or plant, the genotype of which has been altered by the presence of exogenous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

The term "vector" is used in reference to polynucleotide or other molecules that transfer nucleic acid segment(s) into a cell. A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

Markers, Haplotypes, and Marker Profiles Associated with Resistance to Soybean Aphid:

Markers, primers, haplotypes, and marker profiles, and methods of their use for identifying and/or selecting soybean plants with improved soybean aphid resistance, are provided. The method for determining the presence/absence/allele of a particular marker allele associated with soybean aphid resistance and within or linked to a Rag gene or interval in soybean plant or germplasm, and in turn determining the Rag haplotype and/or marker profile of the plant/germplasm, comprises analyzing genomic DNA from a soybean plant or germplasm to determine if at least one, or a plurality, of such markers is present or absent and in whet allelic form. Using this information regarding the Rag-associated markers present in the particular plant or germplasm in turn allows a Rag haplotype to be assigned to that plant/germplasm. If multiple Rag haplotypes are deduced for a plant, a marker profile can in turn be assigned by combining all of these Rag haplotypes.

In certain examples, plants or germplasm are identified that have at least one favorable allele, haplotype, or marker profile that positively correlates with resistance or improved resistance. However, in other examples, it is useful for exclusionary purposes during breeding to identify alleles, haplotypes, or marker profiles that negatively correlate with resistance, for example to eliminate such plants or germplasm from subsequent rounds of breeding.

While any marker linked to a Rag gene or interval is useful, markers that map closer to a Rag gene or interval are generally preferred over markers that map farther from a Rag gene or interval. Marker loci are especially useful when they are closely linked to a Rag gene or interval. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with the Rag gene to which they are linked. Thus, the loci are separated from the Rag gene to which they are linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less.

In certain examples, multiple marker loci that collectively make up the Rag haplotype of interest are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

In certain examples, markers useful for defining a Rag1 haplotype are linked or are closely linked to the interval flanked by and including the marker loci Satt540 and BARC-016783-02329 in the Soybase database (Soybase and the Soybean Breeder's Toolbox website). In other examples, markers useful for defining a Rag1 haplotype are linked or are closely linked to the interval flanked by and including the marker loci BARC-039195-07466 and BARC-016783-02329 in the Soybase database (Soybase and the Soybean Breeder's Toolbox website). In still further examples, markers useful for defining a Rag1 haplotype are within the interval flanked by and including Satt540 and BARC-016783-02329 or BARC-039195-07466 and BARC-016783-02329 in the Soybase database (Soybase and the Soybean Breeder's Toolbox website). In other particular examples, the markers useful for defining a Rag1 haplotype are within the interval flanked by and including Satt435 and Sat_244 in the Soybase database (Soybase and the Soybean Breeder's Toolbox website). In further particular examples, the markers useful for defining a Rag1 haplotype are within the interval flanked by and including physical position 5453161-8194502 on LG-M on the Glyma1 soybean genome assembly.

In additional examples, markers useful for defining a Rag2 haplotype are linked or are closely linked to the interval flanked by and including the marker loci Satt334 and Sat_317 in the Soybase database (Soybase and the Soybean Breeder's Toolbox website). In other examples, markers useful for defining a Rag2 haplotype are linked to or are closely linked to the interval flanked by and including the marker loci BARC-029823-06424 and Sct_033 in the Soybase database (Soybase and the Soybean Breeder's Toolbox website). In still further examples, markers useful for defining a Rag2 haplotype are within the interval flanked by and including Satt334 and Sat_317 or BARC-029823-06424 and Sct_033 in the Soybase database (Soybase and the Soybean Breeder's Toolbox website). In other particular examples, the markers useful for defining a Rag2 haplotype are within the interval flanked by and including Satt334 and Satt510 in the Soybase database (Soybase and the Soybean Breeder's Toolbox website). In further particular examples, the markers useful for defining a Rag2 haplotype are within the interval flanked by and including physical position 28416122-30590233 on LG-F on the Glyma1 soybean genome assembly.

In yet further examples, markers useful for defining a Rag3 haplotype are linked or are closely linked to the interval flanked by and including the marker loci Sat_339 and Sct_065 in the Soybase database (Soybase and the Soybean Breeder's Toolbox website). In still further examples, markers useful for defining a Rag3 haplotype are linked or are closely linked to the interval flanked by and including the marker loci BARC-031195-07010 and Sat_370 in the Soybase database (Soybase and the Soybean Breeder's Toolbox website). In still further examples, markers useful for defining a Rag3 haplotype are within the interval flanked by and including Sat_339 and Sct_065 or BARC-031195-07010 and Sat_370 in the Soybase database (Soybase and the Soybean Breeder's Toolbox website). In other particular examples, the markers useful for defining a Rag3 haplotype are within the interval flanked by and including Sat_339 and Sat_370 in the Soybase database Soybase and the Soybean Breeder's Toolbox website). In further particular examples, the markers useful for defining a Rag3 haplotype are within the interval flanked by and including physical position 4157916-7054678 on LG-J on the Glyma1 soybean genome assembly.

Markers within, linked to, or closely linked to these intervals are illustrated in the genetic map of FIG. 1. Numerous such markers are also well known in the art, for example, are described in the USDA's soybase database (Soybase and the Soybean Breeder's Toolbox website).

Exemplary markers useful for defining Rag haplotypes are provided in Table 1. Also provided in Table 1 are the target regions containing the markers, as well as primers and probes that can be used to amplify and detect the markers.

In certain examples the marker loci used to define the Rag1 haplotype are one or more of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In other examples, the marker loci used to define the Rag1 haplotype are two or more of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In further examples, the marker loci used to define the Rag1 haplotype are three or more of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In additional examples, the marker loci used to define the Rag1 haplotype are four or more of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In still further examples, the marker loci used to define the Rag1 haplotype are five or more of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In yet further examples, the marker loci used to define the Rag1 haplotype are all of S15354-001-Q001, S14181-1-Q1, S13871-1-Q1, S14161-1-Q10, S09515-1-Q1, S14151-1-Q1, S14151-2-Q4, S07164-1-Q12, S14182-1-Q1, S00812-1-A, and S02780-1-A. In a particular example, the marker loci used to define the Rag1 haplotype are all of S14161-1-Q10, S09515-1-Q1, S14151-2-Q4, and S07164-1-Q12.

In certain examples, the marker loci used to define the Rag2 haplotype are one or more of S01190-1-A, S14761-001-Q001, S14771-001-Q001, S07165-1-Q3, S14778-001-Q001, and S01164-1-Q1. In other examples, the marker loci used to define the Rag2 haplotype are two or more of S01190-1-A, S14761-001-Q001, S14771-001-Q001, S07165-1-Q3, S14778-001-Q001, and S01164-1-Q1. In additional examples, the marker loci used to define the Rag2 haplotype are three or more of S01190-1-A, S14761-001-Q001, S14771-001-Q001, S07165-1-Q3, S14778-001-Q001, and S01164-1-Q1. In further examples, the marker loci used to define the Rag2 haplotype are four or more of S01190-1-A, S14761-001-Q001, S14771-001-Q001, S07165-1-Q3, S14778-001-Q001, and S01164-1-Q1. In still further examples, the marker loci used to define the Rag2 haplotype are all of S14761-001-Q001, S14771-001-Q001, S07165-1-Q3, S14778-001-Q001, and S01164-1-Q1. In a particular example, the marker loci used to define the Rag2 haplotype are S07165-1-Q3, S01190-1-A, and S01164-1-Q1.

In certain examples, the marker loci used to define the Rag3 haplotype are one or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In other examples, the marker loci used to define the Rag3 haplotype are two or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In additional examples, the marker loci used to define the Rag3 haplotype are three or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In further examples, the marker loci used to define the Rag3 haplotype are four or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In still further examples, the marker loci used to define the Rag3 haplotype are five or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. examples, the marker loci used to define the Rag3 haplotype are one or more of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In additional examples, the marker loci used to define the Rag3 haplotype are all of S13662-1-Q3/Q6, S13663-1-Q1, S11411-1-Q1, S13664-1-Q1/Q002, S13672-1-Q1/Q2/Q3, S13674-1-Q1/Q007, and S13675-2-Q1. In a particular example, the marker loci used to define the Rag3 haplotype are all of S11411-1-Q1, S13674-1-Q1/Q007, and S13675-2-Q1.

TABLE 1

Selected markers useful for defining Rag haplotypes and marker profiles

| Composite Map Position (cM) | Physical pos. of SNP | Geno- types | Marker | Forward and Reverse Primers | Probes (probe1-FAM/probe2-VIC; SNP base indicated by capital letter) |
|---|---|---|---|---|---|
| Rag1 (LG-M) | | | | | |
| 25.7 cM | 5453161 | A/T | S15354-001-Q1 | SEQ ID NO: 132 ccaaatcagatatcaagatgatggt SEQ ID NO: 133 ggccaagcaatacacaagaaa | SEQ ID NO: 134 atctatgAttccattttt SEQ ID NO: 135 atcatctatgTttccatttt |
| 26.06 cM | 5516385 | A/G | S14181-1-Q1 | SEQ ID: 1 gcatctcatgattaagtag SEQ ID: 2 caagaactttgcttgtcttgctg | SEQ ID: 3 caatcaGcacccttg SEQ ID: 4 aagcaatcaAcacccttt |
| 26.06 cM | 5516818 | C/T | S13871-1-Q1 | SEQ ID: 6 gcaggctcatcagattgctt SEQ ID: 7 gcagcgtctcatcaacaaaa | SEQ ID: 8 ttgaaacCaccattttt SEQ ID: 9 aaacTaccattttgc |
| 26.49 cM | 5598980 | C/G | S14161-1-Q10 | SEQ ID: 11 caccagctcgataagctagagat SEQ ID: 12 ttagccatggattttgttgaatac | SEQ ID: 13 ccagtagcaGcccta SEQ ID: 14 agtagcaCccctaccaa |
| 26.51 cM | 5602544 | A/G | S09515-1-Q1 | SEQ ID: 16 tgcaagattgatttttatgatacgg SEQ ID: 17 ggactaaaattagaaaaagaggaacca | SEQ ID: 18 tattgccaAttcgatcc SEQ ID: 19 tattgccaGttcgatc |
| 26.52 cM | 5605203 | A/C | S14151-1-Q1 | SEQ ID: 21 ccagcttcttttgctccatc SEQ ID: 22 cgacgctcctaagtattggtg | SEQ ID: 23 cattgtacgTccctc SEQ ID: 24 atcattgtacgGccc |
| 26.52 cM | 5605275 | A/G | S14151-2-Q4 | SEQ ID: 26 aatcccacaccagcttcttttt SEQ ID: 27 gtgtggcactgtagcagataaagata | SEQ ID: 28 cagaacaTcttggc SEQ ID: 29 cagaacaCcttggc |
| 26.54 cM | 5608106 | A/G | S07164-1-Q12 | SEQ ID: 31 tcatttcctgatgctcaccata SEQ ID: 32 ggttgtatccatcttctgaactgc | SEQ ID: 33 ttgagaaaacGtctgca SEQ ID: 34 ttgagaaaacAtctgca |
| 26.6 cM | 5630404 | A/G | S14182-1-Q1 | SEQ ID: 36 tgtactttggctgcgtctcc SEQ ID: 37 ggtaactcctttgtaatgttcaccac | SEQ ID: 38 ccatgtcaaTgcc SEQ ID: 39 ccatgtcaaCgcca |
| 33.2 cM | 6754454 | C/G | S00812-1-A | SEQ ID: 41 gctgctcttttctctgctgtgatca SEQ ID: 42 tgggtggtttccttgtttataccaac | SEQ ID: 43 tataccCgtgagactat SEQ ID: 44 tataccGgtgagactat |
| 34.2 cM | 6671535 | A/G | S02780-1-A | SEQ ID: 46 ggcatttgcttcaattttcc SEQ ID: 47 acttttgccccatatakgatatgc | SEQ ID: 48 actctggAtaacctg SEQ ID: 49 actctggGtaacctg |
| Rag2 (LG-F) | | | | | |
| 72.08 | 28187733 | A/T | S01190_1-A | SEQ ID: 127 ttcagctccccattatttcg SEQ ID: 128 ttggccaacctatcctcaac | SEQ ID: 129 tcagctcaTttttgt SEQ ID: 130 cagctcaCttttgt |

TABLE 1-continued

Selected markers useful for defining Rag haplotypes and marker profiles

| Composite Map Position (cM) | Physical pos. of SNP | Geno-types | Marker | Forward and Reverse Primers | Probes (probe1-FAM/probe2-VIC; SNP base indicated by capital letter) |
|---|---|---|---|---|---|
| 72.85 | 28829625 | A/G | S14761-001-Q001 | SEQ ID: 51 agagagcaacaaccagtaatttcata<br>SEQ ID: 52 acttagtgcatctattgcaaccac | SEQ ID: 53 ccactaaAgttagcctag<br>SEQ ID: 54 ccactaaGgttagcctag |
| 72.85 | 28837383 | C/T | S14771-001-Q001 | SEQ ID: 56 ccttcaacaacagcagctttaat<br>SEQ ID: 57 ctgcttaatcgactgagctagacc | SEQ ID: 58 cattagatcaaacaCtgc<br>SEQ ID: 59 cattagatcaaacaTtgc |
| 73.0 cM | 29097652 | A/T | S07165-1-Q3 | SEQ ID: 61 gcttgtaagctattcccaaacg<br>SEQ ID: 62 tatctgtgagcggttgcttg | SEQ ID: 63 tttcttatcTaaggttttg<br>SEQ ID: 64 ttccttatcAaaggttttg |
| 73.2 | 29678319 | C/T | S14778-001-Q001 | SEQ ID: 66 tgaggatatttatggaatttgtcaga<br>SEQ ID: 67 catgatgagatcagaaaagaaatgc | SEQ ID: 68 cttataaaacCgctttc<br>SEQ ID: 69 cttataaaacTgctttcc |
| 73.2 cM | 29825175 | C/G | S01164-1-Q1 | SEQ ID: 71 gacagtggagagttacgagga<br>SEQ ID: 72 cacatctgaatcaccctgga | SEQ ID: 73 ccacctacatCactac<br>SEQ ID: 74 ccacctacatGactac |
| Rag3 (JG-J) | | | | | |
| 37.8800 | 5140274 | A/G | S13662-1-Q3<br>S13662-1-Q6 | SEQ ID: 76 tctttatgatgatgagcagaagcta<br>SEQ ID: 77 caccccaaaaacaaaacactc<br>SEQ ID: 80 gggaagagtctgaatggtgtct<br>SEQ ID: 81 ccccaaaaacaaaacactcatc | SEQ ID: 78 ctttcagAgcattagc<br>SEQ ID: 79 tttgctttcagGgcat<br>SEQ ID: 82 ctttcagAgcattagc<br>SEQ ID: 83 tttgctttcagGgcat |
| 41.7323 | 5919650 | T/C | S13663-1-Q1 | SEQ ID: 85 tctgatgatgattatagtgggctct<br>SEQ ID: 86 tgctatgcatttgaaaccaca | SEQ ID: 87 ctgataacaaTagccc<br>SEQ ID: 88 ataacaaCagccctgact |
| 41.96 | 5960726 | C/G | S11411-1-Q1 | SEQ ID: 90 ggacccaacatcaatcaaatg<br>SEQ ID: 91 tgcattctggaaagacatgg | SEQ ID: 92 ttttctgCactccc<br>SEQ ID: 93 ttttctgGactccc |
| 42.5533 | 6066531 | T/G | S13664-1-Q1<br>S13664-1-Q002 | SEQ ID: 95 catgccagtatgaatgtgctg<br>SEQ ID: 96 tccgcacatttagttccctta<br>SEQ ID: 99 caaagtgtcatgccagtatgaatg<br>SEQ ID: 100 gttttatttcattccgcacatttag | SEQ ID: 97 attgtgacactctatTgc<br>SEQ ID: 98 ttgtgacactctatGgca<br>SEQ ID: 101 attgtgacactctatTgc<br>SEQ ID: 102 ttgtgacactctatGgca |
| 419757 | 6231641 | G/A | S13672-1-Q1<br>S13672-1-Q2<br>S13672-1-Q3 | SEQ ID: 104 gatcggttcccaaactagca<br>SEQ ID: 105 aacatgcaaaatgcaccaag<br>SEQ ID: 108 cggttcccaaactagcaggt<br>SEQ ID: 109 tgcaaaatgcaccaagttagat<br>SEQ ID: 110 agatcggttcccaaactagcag<br>SEQ ID: 111 catgcaaaatgcaccaagtta | SEQ ID: 106 cagttgattactCtgc<br>SEQ ID: 107 cagttgattactTtgc<br>SEQ ID: 106 cagttgattactCtgc<br>SEQ ID: 107 cagttgattactTtgc<br>SEQ ID: 112 cagttgattactCtgc<br>SEQ ID: 113 cagttgattactTtgc |
| 43.7295 | 6524877 | C/G | S13674-1-Q1<br>S13674-1-Q007 | SEQ ID: 115 ccaccattaccccctctcctt<br>SEQ ID: 116 acctagcattgcaatctcttcc<br>SEQ ID: 119 ttaccccctctcctttctcaacatta<br>SEQ ID: 120 tgcaatctcttccaagctagaact | SEQ ID: 117 ttggcattcaGccc<br>SEQ ID: 118 tttggcattcaCccc<br>SEQ ID: 117 ttggcattcaGccc<br>SEQ ID: 118 tttggcattcaCccc |
| 43.8186 | 6542422 | G/A | S13675-2-Q1 | SEQ ID: 122 aggtggtggcagtgttgatt<br>SEQ ID: 123 ctccaacatggctgtgctaa | SEQ ID: 124 aaccgtggctCatt<br>SEQ ID: 125 caaaccgtggctTat |

Selected haplotypes that are based upon the markers in Table 1 are described in Table 2.

TABLE 2

Selected Rag haplotypes generated using the selected markers
Rag Haplotypes

Rag1

| S14161-1-Q10 | S09515-1-Q1 | S14151-2-Q4 | S07164-1-Q12 | Haplotype |
|---|---|---|---|---|
| C | G | G | G | Rag1-a |
| G | A | G | A | Rag1-b |
| C, G | A | A | A | Rag1-c |
| C | G | A | A | Rag1-d |
| C | A | A | A | Rag1-e |
| G | A | A | A | Rag1-f |
| C | A, G | G | A | Rag1-g |

Rag2

| S07165-1-Q3 | S01190-1-A | S01164-1-Q1 | Haplotype |
|---|---|---|---|
| A | C | C | Rag2-a |
| T | T | G | Rag2-b |
| T | C | C | Rag2-c |
| A | T | G | Rag2-d |
| T | C | G | Rag2-f |

Rag3

| S11411-1-Q1 | S13674-1-Q1/Q007 | S13675-2-Q1 | Haplotype |
|---|---|---|---|
| C | C | G | Rag3-a |
| G | C | G | Rag3-b |
| G | G | A | Rag3-c |
| G | G | G | Rag3-d |

In addition to the markers discussed herein, information regarding useful soybean markers can be found, for example, on the USDA's Soybase website, available at www.soybase.org. One of skill in the art will recognize that the identification of favorable marker alleles may be germplasm-specific. The determination of which marker alleles correlate with resistance (or susceptibility) is determined for the particular germplasm under study. One of skill will also recognize that methods for identifying the favorable alleles are routine and well known in the art, and furthermore, that the identification and use of such favorable alleles is well within the scope of the invention.

In some examples marker profiles comprising two or more Rag haplotypes are provided. For instance, in one example, a particular Rag1 haplotype and a particular Rag2 haplotype define the marker profile of a particular plant. In another example, a particular Rag1 haplotype and a particular Rag3 haplotype define the marker profile of a particular plant. In a still further example, a particular Rag2 haplotype and a particular Rag3 haplotype define the marker profile of a particular plant. In an additional example, a particular Rag1 haplotype, a particular Rag2 haplotype, and a particular Rag3 haplotype define the marker profile of a particular plant. More specifically, a particular plant marker profile might be, for example, Rag1-a/Rag2-b or Rag1-b/Rag2-a/Rag3-c.

Marker Assisted Selection:

The use of marker assisted selection (MAS) to select a soybean plant or germplasm which has a certain Rag haplotype or marker profile is provided. For instance, in certain examples a soybean plant or germplasm possessing a certain predetermined favorable Rag haplotype will be selected via MAS. In certain other examples, a soybean plant or germplasm possessing a certain predetermined favorable marker profile will be selected via MAS.

Using MAS, soybean plants or germplasm can be selected for markers or marker alleles that positively correlate with resistance, without actually raising soybean and measuring for resistance or improved resistance (or, contrawise, soybean plants can be selected against if they possess markers that negatively correlate with resistance or improved resistance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

Nucleic Acid Amplification Methods:

In some examples, the molecular markers are detected using a suitable amplification-based detection method. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter, et al. (1984) Nucleic Acids Res. 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair or probe. For example, primers can be designed using any suitable software program, such as LASERGENE® or Primer3.

It is not intended that the primers be limited to generating an amplicon of any particular size. For example, the primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length.

PCR, RT-PCR, and LCR are in particularly broad use as amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous journal and patent references, such as Mullis, et al. (1987) U.S. Pat. No. 4,683,202; Arnheim & Levinson (Oct. 1, 1990) C&EN 36-47; Kwoh, et al. (1989) Proc. Natl. Acad. Sci. USA 86:1173; Guatelli, et al., (1990) Proc. Natl. Acad. Sci. USA 87:1874; Lomell, et al, (1989) J. Clin. Chem 35:1826; Landegren, et al, (1988) Science 241:1077-1080; Van Brunt, (1990) Biotechnology 8:291-294; Wu and Wallace, (1989) Gene 4:560; Barringer, et al, (1990) Gene 89:117, and Sooknanan and Malek, (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype SNP alleles are provided. For example, exemplary primers and probes are provided in Table 1, as are the target regions to which these primers and probes hybridize. However, one of skill will immediately recognize that other primer and probe sequences could also be used. For instance primers to either side of the given primers can be used in place of the given primers, so long as the primers can amplify a region that includes the allele to be detected, as can primers and probes directed to other SNP marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and calorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Detectable labels may also include reporter-quencher pairs, such as are employed in Molecular Beacon and TaqMan™ probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent, depending on the embodiment. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, *Handbook of Fluorescent Probes and Research Chemicals,* Molecular Probes of Eugene, Oreg., 1992, the content of which is incorporated herein by reference.

In certain examples, reporter-quencher pairs are selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAMT™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY7™, QSY9™, QSY-21™ and QSY35™, each of which are available from Molecular Probes, Inc., and the like.

In one aspect, real time PCR or LCR is performed on the amplification mixtures described herein, e.g., using molecular beacons or TaqMan™ probes. A molecular beacon (MB) is an oligonucleotide which, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone, et al., (1995) Molecular beacon probes combined with amplification by NASBA enable homogenous real-time detection of RNA, Nucleic Acids Res. 26:2150-2155; Tyagi and Kramer, (1996) Molecular beacons: probes that fluoresce upon hybridization, Nature Biotechnology 14:303-308; Blok and Kramer, (1997) Amplifiable hybridization probes containing a molecular switch, Mol Cell Probes 11:187-194; Hsuih. et al., (1997) Novel, ligation-dependent PCR assay for detection of hepatitis C in serum, J Clin Microbiol 34:501-507; Kostrikis, et al., (1998) Molecular beacons: spectral genotyping of human alleles, Science 279:1228-1229; Sokol, et al., (1998) Real time detection of DNA:RNA hybridization in living cells, Proc. Natl. Acad. Sci. U.S.A. 95:11538-11543; Tyagi, et al., (1998) Multicolor molecular beacons for allele discrimination, Nature Biotechnology 16:49-53; Bonnet, et al., (1999) Thermodynamic basis of the chemical specificity of structured DNA probes, Proc. Natl. Acad. Sci. U.S.A. 96:6171-6176; Fang, et al. (1999) Designing a novel molecular beacon for surface-immobilized DNA hybridization studies, J. Am. Chem. Soc. 121:2921-2922; Marras, et al., (1999) Multiplex detection of single-nucleotide variation using molecular beacons, Genet. Anal. Biomol. Eng. 14:151-156; and Vet, et al., (1999) Multiplex detection of four pathogenic retroviruses using molecular beacons, Proc. Natl. Acad. Sci. U.S.A. 96:6394-6399. Additional details regarding MB construction and use is found in the patent literature, e.g., U.S. Pat. Nos. 5,925,517; 6,150,097; and 6,037,130.

Another real-time detection method is the 5'-exonuclease detection method, also called the TaqMan™ assay, as set forth in U.S. Pat. Nos. 5,804,375; 5,538,848; 5,487,972; and 5,210,015, each of which is hereby incorporated by reference in its entirety. In the TaqMan™ assay, a modified probe, typically 10-25 nucleic acids in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook, et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel, et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis, et al., eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH). ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Real-Time SNP Detection Assays:

Real-time amplification assays, including MB or TaqMan™ based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 11-20 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, for instance the target regions listed in Table 1, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a particular SNP locus associated with aphid resistance). Illumina® detection systems utilize similar technology in a fixed platform format. The fixed platform utilizes a physical plate that can be created with up to 384 markers. The Illumina® system is created with a single set of markers that cannot be changed and utilizes dyes to indicate marker detection.

These systems and methods represent a wide variety of available detection methods which can be utilized to detect markers associated with improved aphid resistance, but any other suitable method could also be used.

Stacking Desired Rag Alleles, Haplotypes, or Marker Profiles:

Methods of stacking desired Rag alleles, haplotypes, or marker profiles are provided, as are methods of detecting soybean plants or germplasm that possess stacked alleles, haplotypes, or marker profiles. In order to stack desired alleles, haplotypes, or marker profiles, two or more plants with different desired alleles, haplotypes, or marker profiles are first identified. Following identification of the desired alleles, haplotypes, or marker profiles, any method for introgressing an allele, haplotype, or marker profile into soybean plants known to one of skill in the art can be used, including breeding and transgenic methods. Typically, a first soybean germplasm that contains a desired allele, haplotype, or marker profile and a second soybean germplasm that contains a different desired allele, haplotype, or marker profile are provided. The first soybean germplasm may be crossed with the second soybean germplasm to provide progeny soybean germplasm. These progeny germplasm are screened to determine the presence of the desired phenotype and or the presence of both of the desired alleles, haplotypes, or marker profiles, and progeny that test positive for the presence of the desired alleles, haplotypes, or marker profiles are selected. Methods for performing such screening are well known in the art and any suitable method can be used. In certain examples, the stacked plants can also be self-crossed in order to generate homozygosity.

Phenotypic Screening for Soybean Aphid Resistant Soybean Plants:

Three types of soybean aphid resistance have been described: antibiosis, antixenosis, and tolerance. Experienced plant breeders can recognize resistant soybean plants in the field, and can select the resistant individuals or populations for breeding purposes or for propagation. In this context, the plant breeder recognizes "resistant" and "non-resistant" or "susceptible" soybean plants. However, plant resistance is a phenotypic spectrum consisting of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for resistance populations, and to use introgression techniques to breed a resistance trait into an elite soybean line, for example.

To that end, screening and selection of resistant soybean plants may be performed, for example, by exposing plants to soybean aphid in a live aphid assay and selecting those plants showing resistance to aphids. The live aphid assay may be any such assay known to the art, e.g., as described in Hill, C. B., et al., Resistance to the soybean aphid in soybean germplasm, (2004) Crop Science 44:98-106, Hill, C. B., et al., Resistance of Glycine species and various cultivated legumes to the soybean aphid (Homoptera: Aphididae), (2004) J. Economic Entomology 97:1071-1077, or Li, Y., et al., Effect of three resistant soybean genotypes on the tecunalry, mortality, and maturation of soybean aphid (Homoptera: Aphididae), (2004) J. Economic Entomology 97:1106-1111, or as described in the Examples hereof.

One example of an antixenosis resistance assay includes placing aphids or aphid-infested plant parts on VC or V1 stage plants and rating aphid population and plant damage weekly. For example, in certain examples, numerous viviparous alate adult females are placed on newly expanded unifoliates with a moistened camel's hair paintbrush, the plants are arranged in a randomized design within a tray, and the aphid resistance is evaluated at 7 and 14 days after infestation, using an antixenosis rating scale. One example of such an antixenosis scale is a 1-9 rating scale wherein:

9=Equivalent or better when compared to a resistant check—No aphids on the plant;
7=Very little damage, only a few aphids found on the plant;
5=Moderately Susceptible;
3=Major damage, including stunting and foliar stress; and
1=Plants are completely covered—Severe damage, including severe stunting and necrosis; equivalent or worse when compared to a susceptible check.

One example of an antibiosis resistance assay includes placing one double-sided sticky cage containing two alate adult females on each unifoliate of plants at the V1 stage and then placing a piece of organdy cloth over the cage to restrict the aphids' movements. This is done for both the plant variety to be tested and a plant variety known to be susceptible. The aphids are then allowed to reproduce for 96 hours and, at the end of this period, the cages are removed and counts performed on the surviving and deceased aphids to determine the antibiosis resistance of the plants tested. Plants with a high rate of nymphal production are classified as susceptible. Plants with some nymphs, but with statistically lower nymphal populations compared to the susceptible check are classified as moderately resistant. Plants with no nymph production within the sticky cages and dead or unhealthy in appearance adults are classified as resistant.

Automated Detection/Correlation Systems, Kits, and Nucleic Acids:

In some examples, a kit or an automated system for detecting markers, Rag haplotypes, and marker profiles, and/or correlating the markers, Rag haplotypes, and marker profiles with a desired phenotype (e.g., resistance) are provided. Thus, a typical kit or system can include a set of marker probes or primers configured to detect at least one favorable allele of one or more marker locus associated with resistance or improved resistance to a soybean aphid infestation, for instance a favorable Rag haplotype or marker profile. These probes or primers can be configured, for example, to detect the marker alleles noted in the tables and examples herein, e.g., using any available allele detection format, such as solid or liquid phase array based detection, microfluidic-based sample detection, etc. The systems and kits can further include packaging materials for packaging the probes, primers, or instructions, controls such as control amplification reactions that include probes, primers or template nucleic acids for amplifications, molecular size markers, or the like.

A typical system can also include a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System or kit instructions that describe how to use the system or kit or that correlate the presence or absence of the favorable allele with the predicted resistance are also provided. For example, the instructions can include at least one look-up table that includes a correlation between the presence or absence of the favorable alleles, haplotypes, or marker profiles and the predicted resistance or improved resistance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted resistance or improved resistance. The instructions also typically include instructions providing a user interface with the system, e.g., to permit a user to view results of a sample analysis and to input parameters into the system.

Isolated nucleic acids comprising a nucleic acid sequence coding for resistance to soybean aphid, or sequences complementary thereto, are also included. In certain examples, the isolated nucleic acids are capable of hybridizing under stringent conditions to nucleic acids of a soybean cultivar resistant to soybean, for instance to particular SNPs that comprise a Rag haplotype or marker profile. Vectors comprising such nucleic acids, expression products of such vectors expressed in a host compatible therewith, antibodies to the expression product (both polyclonal and monoclonal), and antisense nucleic acids are also included.

As the parental line having soybean aphid resistance, any line known to the art or disclosed herein may be used. Also included are soybean plants produced by any of the foregoing methods. Seed of a soybean germplasm produced by crossing a soybean variety having a Rag haplotype or marker profile associated with soybean aphid resistance with a soybean variety lacking such Rag haplotype or marker profile, and progeny thereof, is also included.

The present invention is illustrated by the following examples. The foregoing and following description of the present invention and the various examples are not intended to be limiting of the invention but rather are illustrative thereof. Hence, it will be understood that the invention is not limited to the specific details of these examples.

EXAMPLES

Aphid Colonies

The four biotype colonies of soybean aphids are maintained in a growth chamber at the Dallas Center Containment Facility (Dallas Center, Iowa). The colonies are maintained on a continuous supply of soybean variety 90M60. Two colonies of Urbana, Ill. (biotype 1) and Wooster, Ohio (biotype 2) were obtained from Brian Diers at the University of Illinois. Biotype 3 (Indiana) was obtained from Curtis B. Hill at the University of Illinois. Lime Springs, Iowa (biotype X) was collected from soybean fields in Limes Springs, Iowa. The colonies are maintained in isolated tents to avoid mixing.
Rag1-a/Rag2-b Stack A population of 736 segregating plants was developed by crossing plants that carried (Rag-1a) from 95B97 and LD08-89051a (Rag2-b). The progeny were screened with the four biotypes to determine the efficacy of the stack compared to the single gene resistance. The 95B97 and LD08-89051a donors possess antibiosis resistance to some of the biotypes (Table 3).
Choice Bioassay (Antixenosis):

The choice tests were conducted in a growth chamber with temperatures between 22 and 25° C. with a 16 hour photoperiod. The segregating population was planted in Cone-tainers™ (Stuewe and Sons, Inc., Tangent, Oreg.) and infested at the V1 growth stage. Seven viviparous apterous adult females were placed on the newly expanded unifoliates with a moistened camel's hair paintbrush. The plants were arranged in completely randomized design within a tray including a susceptible cheek and the two resistant donor lines. The trays were placed within a water bath inside a Bioquip tent to isolate the aphids. The trays were watered from the bottom to avoid disrupting the aphid feeding. The aphid resistance was evaluated at 7 and 14 days after infestation, using a 1-9 antixenosis rating.
    9=Equivalent or better when compared to the resistant check—No aphids on the plant
    7=Very little damage, only a few aphids found on the plant.
    5=Moderately Susceptible
    3=Major damage, including stunting and foliar stress
    1=Plants are completely covered. Severe damage, including severe stunting and necrosis; equivalent or worse when compared to the susceptible
Non-Choice Bioassay (Antibiosis):

At the same time the plants were infested in the antixenosis bioassay, the antibiosis bioassay was conducted. To determine antibiosis resistance, a non-choice test was conducted (i.e., a test wherein the aphids have no choice but to either feed on the plant or starve to death). The non-choice bioassay was conducted using the same environmental conditions as described above in the choice bioassay. At the V1 stage, one double-sided sticky cage was placed on each unifoliate. Using a moistened paintbrush, two viviparous apterous adult females were placed within the cage and a piece of organdy cloth was placed over the cage to restrict the aphids' movements. The aphids were allowed to reproduce for 7 days and then the survival, death, and fecundity of the aphids within the cage were recorded. The fecundity was calculated as the mean number of surviving nymphs produced within a cage during the 96 hour period for each plant introduction. Plants that had a high rate of nymphal production were classified as susceptible. Plants with some nymphs, but with statistically lower populations compared to the susceptible check were classified as moderately resistant. Plants with no nymph production within the sticky cages and dead or unhealthy in appearance adults were classified as resistant. The 736 were leaf punched to determine the genotypic class.

TABLE 3

Aphid resistance phenotype and genotype data for selected PIs

| Variety | MG | Country of Origin | Antibiosis Results | | | | | Antixenosis Results | | | | | Rag Haplotype |
|---|---|---|---|---|---|---|---|---|---|---|---|---|---|
| | | | 1 | 2 | 3 | X | Y | 1 | 2 | 3 | X | Y | |
| 95B97 | | Pioneer | R | S | M | R | S | R | S | M | R | S | Rag1-a |
| Dowling | VIII | US | R | S | M | R | S | R | S | M | R | S | Rag1-a |
| LD08-89068a | III | Illinois | R | R | S | S | S | R | R | S | S | S | Rag2-b |
| PI200538 | VIII | Japan | R | R | S | S | S | R | R | S | S | S | Rag2-b |
| Rag1/Rag2 stack | | US | R | R | R | R | S | R | R | R | R | S | Rag1-a & Rag2-b |
| PI567666 | IV | China | R | R | R | R | R | R | R | R | R | R | Rag1-b & Rag3-b |
| PI567622 | IV | China | R | R | R | R | R | R | R | R | R | R | Rag1-b & Rag3-b |
| PI219652 | VII | Indonesia | S | S | S | S | S | R | R | R | R | R | Rag1-c & Rag3-d |
| PI219655 | VII | Indonesia | S | S | S | S | S | R | R | R | R | R | Rag1-c & Rag3-d |

These results demonstrate that stacking Rag haplotypes results in an unexpected synergistic effect. For instance, while neither the Rag1-a nor the Rag2-b donors exhibited a resistant antibiosis or antixenosis phenotype in regards to biotype 3, the Rag1-a/Rag2-b stack plants did exhibit a resistant phenotype to biotype 3 in both the antibiosis and antixenosis assays.

What is claimed is:

1. A method of improving resistance to one or more soybean aphid biotypes in a soybean plant, line, or strain, the improved resistance comprising one or more of improved antibiosis resistance and improved antixenosis resistance; the method comprising:
   a) identifying in a first soybean plant or soybean germplasm, or a soybean progeny thereof, a favorable allele of at least one marker of comprising S07165-1-Q3;
   b) selecting said first soybean plant, soybean germplasm, or soybean progeny from step a);
   c) identifying in a second soybean plant or soybean germplasm, or a soybean progeny thereof, a favorable allele of at least one marker of at least one Rag gene, wherein said Rag gene is selected from the group consisting of Rag1, Rag2, and Rag3;
      wherein said Rag gene of said second soybean plant, soybean germplasm, or soybean progeny is different than the Rag gene of said first soybean plant, soybean germplasm, or soybean progeny;
   d) selecting said second soybean plant, soybean germplasm, or soybean progeny from step c); and
   e) crossing said first soybean plant, soybean germplasm, or soybean progeny with said second soybean plant, soybean germplasm, or soybean progeny, wherein said crossing produces a soybean progeny comprising (i) said favorable allele of the at least one marker from said first soybean plant, soybean germplasm, or soybean progeny; and (ii) said favorable allele of the at least one marker from said second soybean plant, soybean germplasm, or soybean progeny.

2. The method of claim 1, wherein said first soybean plant, soybean germplasm, or soybean progeny and said second soybean plant, soybean germplasm, or soybean progeny collectively comprise a favorable allele of a marker of all three of Rag1, Rag2, and Rag3.

3. The method of claim 1, wherein the improved soybean aphid resistance comprises both improved antibiosis resistance and improved antixenosis resistance.

4. The method of claim 1, wherein the improved soybean aphid resistance comprises improved resistance to at least two soybean aphid biotypes.

5. The method of claim 1, wherein the improved soybean aphid resistance comprises improved resistance to at least three soybean aphid biotypes selected from the group consisting of biotype 1, biotype 2, biotype 3, biotype X, and biotype Y.

6. The method of claim 1, wherein the identification further comprises detecting each said favorable allele, said detecting step comprising amplifying a nucleic acid sequence comprising said marker of each said favorable allele and detecting the resulting amplified nucleic acid sequence comprising each said marker.

7. The method of claim 6, wherein the amplifying comprises performing a polymerase chain reaction (PCR) using one or more nucleic acids from the plant as a template in the PCR.

8. The method of claim 1, wherein said marker of a) is linked to a Rag2-b haplotype.

9. The method of claim 6, wherein said amplifying comprises amplification of SEQ ID NO:65.

10. The method of claim 9, wherein said amplification comprises providing one or more nucleic acid primers, wherein said primers comprise the nucleic acid sequence selected from the group consisting of SEQ ID NOs: 61 and 62.

11. The method of claim 10, wherein said detecting further comprises hybridization with one or more nucleic acid probes, wherein said probes comprise the nucleic acid sequence selected from the group consisting of SEQ ID NOs: 63 and 64.

12. The method of claim 1, wherein the favorable allele of a) further comprises at least one marker of at least one Rag gene, wherein said Rag gene is selected from the group consisting of Rag1 and Rag3.

* * * * *

SEQUENCE LISTING

```
<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 1
gcatctcatg attaagtagg                                                   20

<210> SEQ ID NO 2
<211> LENGTH: 23
<212> TYPE: DNA
<213> ORGANISM: Artificial Sequence
<220> FEATURE:
<223> OTHER INFORMATION: Primer/Probe/Target Sequence

<400> SEQUENCE: 2
caagaacttt gcttgtcttg ctg                                               23

<210> SEQ ID NO 3
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 3
caatcagcac ccttg                                                        15

<210> SEQ ID NO 4
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 4
aagcaatcaa caccctt                                                      17
```

<210> SEQ ID NO 5
<211> LENGTH: 728
<212> TYPE: DNA
<213> ORGANISM: Glycine max
<220> FEATURE:
<221> NAME/KEY: misc_feature
<222> LOCATION: (28)..(28)
<223> OTHER INFORMATION: n is a, c, g, or t

<400> SEQUENCE: 5

```
aggsaraaky cacactataa tggaaganca cctgaatggc ctatgaggct tctctaaaac     60
agcagagaag aacatttcct gctcatcctt atcaagcttt ggaacaacca cccatttgtg    120
cttcttatac ctcagcattt tgaaggcctg caagtaatca tacaaatcta ccttcaagca    180
gaaaaagctg tcaatccaaa gcaayccccc tggcctcaga actctatccc aatcatacaa    240
tataaactca aggagcacaa gatcaatcca cccatcaaga aaccttgttg tgtgaatcaa    300
atctagggtg ttgtcaaaaa atggaagcct tggtttata gtcaagtara gaggaacaag     360
tcctcttaga gcaatcattt cattgaaggg tgctccaaaa ttgatattgg ctgaaactat    420
agtcacattg aattccctca tcctagcagc aaaartccca gttccaacac ttaagtccaa    480
tcctataagg aaaatctgct gtgcggtctg aatcagcttc caggcttacc catcttggca    540
tctcatgatt ggtgaggttg aagcaatcar caccccttgaa gaatccctta cgagtggcat    600
tgccagcaag acaagcaaag ttcttgcact ggtattgact ccatctgaca tttctatcat    660
cagggagttt ccacaaggat tcattgacgg gaaatggttg tttgtatagc ttaggggatc    720
tgaaaagc                                                            728
```

<210> SEQ ID NO 6
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 6
gcaggctcat cagattgctt                                                20

<210> SEQ ID NO 7
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 7
gcagcgtctc atcaacaaaa                                                20

<210> SEQ ID NO 8
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 8 ttgaaccac catttt                                                     16

<210> SEQ ID NO 9
<211> LENGTH: 15
<212> TYPE: DNA

```
<213> ORGANISM: Artificial Sequence
<220> FEATURE:
<223> OTHER INFORMATION: Primer/Probe/Target Sequence

<400> SEQUENCE: 9
aaactaccat tttgc                                                          15

<210> SEQ ID NO 10
<211> LENGTH: 726
<212> TYPE: DNA
<213> ORGANISM: Glycine max
<220> FEATURE:
<221> NAME/KEY: misc_feature
<222> LOCATION: (658)..(658)
<223> OTHER INFORMATION: n is a, c, g, or t

<400> SEQUENCE: 10
tttctatcat cagggagttt ccacaaggat tcattgacgg gaaatggttg tttgtatagc          60
ttaggggatc ttgaaaagca ccttctccta ggtaaaggat cacagccatg aaccataagc         120
ttttgagcca gtttccagtc atcgttgcag atctcaccaa catcataatc catgtattct         180
tctagctctt ccttcatggc aaagcacgtg tgtcctatgc tggtgaagct tgcattttcc         240
cccataaaat tttgttttcc taatctgtta ggtttgatcc taacatactt gcgaatctct         300
tctcgcagaa agtagtcagc aggctcatca gattgcttct tttttgttga aacctaccat         360
tttgctgatt attgccttca ttttgttgat gagacgctgc cgccgactca agaagtccta         420
atatatcaga aagaaatgca ccttgctgga atacagatgg ggtcaatgat ggatcctgtt         480
ttgtttccct cagtttgtcc agttcctctt caattttctg aattaccatt tcaacagttt         540
tcatcagcac ctcattttga ttcccatttg ggacctcagg attcagagat tgacacacca         600
ttttagtgat tgctcaacaa ataaacagag ataaattgac acatatccca cgcatacnaa         660
taaacagaga ttgacacacc attttagtga ttgctcaaca aatacttaat atcaatatgc         720
aaaaaa                                                                   726

<210> SEQ ID NO 11
<211> LENGTH: 23
<212> TYPE: DNA
<213> ORGANISM: Artificial Sequence
<220> FEATURE:
<223> OTHER INFORMATION: Primer/Probe/Target Sequence

<400> SEQUENCE: 11
caccagctcg ataagctaga gat                                                 23

<210> SEQ ID NO 12
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 12
ttagccatgg attttgttga atac                                                24

<210> SEQ ID NO 13
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 13
```
ccagtagcag cccta                                                    15

<210> SEQ ID NO 14
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 14
agtagcaccc ctaccaa                                                  17

<210> SEQ ID NO 15
<211> LENGTH: 702
<212> TYPE: DNA
<213> ORGANISM: Glycine max
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (494)..(494)
<223> OTHER INFORMATION: n is a, c, g, or t
<220> FEATURE:
<221> NAME/KEY: misc_feature
<222> LOCATION: (569)..(570)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t

<400> SEQUENCE: 15
agcttcgtga agaagtatag gagaggcttc tctccatgaa gggcggttac ttccaaattg    60
ggatcattat tgatgtaatt tttgttagtt tggatgcttg ggtagtcatt gggagcttag   120
attratttgt gaatttcgca aagtgtagaa tmgcaccagc tcgataagct agagattgag   180
ctagcccacc gagagcaaac cttcagagtt ataactagct agctaattaa gccagtagca   240
sccctaccaa gcgacacatt catagsttct ctttaggttt gtattcaaca aaatccatgg   300
ctaagytaga ggctattata aataaactva ggcgagtaac caraatttat tttagaggac   360
tagctatagc aaggcttgtg gctaagccag ttaccttcct gagagtgaac ttgagaaagt   420
acagaggcta gctaaggtag gtattagtct ncctaaacct rattatgctg aaagtctatg   480
tttgnttaat tgtnttttcct ccttgtttcc tttggatwtt ttttatttgc ttggtacttt   540
gtgatgttaa ttattgttga tawtggtann atcatatgta ttttntatca tgtgattgtt   600
gcatatgctt ggnattgtat gttacgatga accctgtaaa ataaagata cttaaaawta    660 tacctatatc tctnataaaa aggtggagag tttccttaaa gg                     702

<210> SEQ ID NO 16
<211> LENGTH: 25
<212> TYPE: DNA

<213> ORGANISM: Artificial Sequence
<220> FEATURE:
<223> OTHER INFORMATION: Primer/Probe/Target Sequence

<400> SEQUENCE: 16
tgcaagattg atttttatga tacgg                                           25

<210> SEQ ID NO 17
<211> LENGTH: 27
<212> TYPE: DNA
<213> ORGANISM: Artificial Sequence
<220> FEATURE:
<223> OTHER INFORMATION: Primer/Probe/Target Sequence

<400> SEQUENCE: 17
ggactaaaat tagaaaaaga ggaacca                                         27

<210> SEQ ID NO 18
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 18
tattgccaat tcgatcc                                                    17

<210> SEQ ID NO 19
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 19
tattgccagt tcgatc                                                     16

<210> SEQ ID NO 20
<211> LENGTH: 402
<212> TYPE: DNA
<213> ORGANISM: Glycine max

<400> SEQUENCE: 20
ttgttaacac gtgataatat tcattagcaa ctacacttag aaactaaata aatataattg      60
acrtactatt gatcatcata aaattaatat tttctaatta akaaaatttt gctaaagaat     120
tagctcttgc tcactttgtc tgatttaacc rgttctttgc aagattgatt tttatgatac     180
ggaattgact ggtattgcca agttcgatcc ggccaatttg gttaagttct acttctaaca     240
ataggctaaa atatttttt tcccttgtaa gttaggattt tttttatttt tggttcctct      300
ttttctaatt ttagtccttg gaaattgttt ttttttttaat tttaatcctt ataagatatt    360
ttattatttt taattcttat aaaattatat atatttttta tt                        402

<210> SEQ ID NO 21
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 21
ccagcttctt ttgctccatc                                                 20

```
<210> SEQ ID NO 22
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 22
cgacgctcct aagtattggt g                                              21

<210> SEQ ID NO 23
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 23
cattgtacgt ccctc                                                     15

<210> SEQ ID NO 24
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 24
atcattgtac ggccc                                                     15

<210> SEQ ID NO 25
<211> LENGTH: 714
<212> TYPE: DNA
<213> ORGANISM: Glycine max

<400> SEQUENCE: 25
tttctgatat ttatcatact aaacgaagca ttaacctcca aatctcctct tagtaatgta    60
ttcttagaaa atagagaatc taattcatca cactctttct catcacatac tggctcggat   120
gcttgtggcc catttcattg gaaaggttct ctagaaatca agataatgtt tagcaaatca   180
aagaacgaga ttctgtttgc tggagcagag ggagatttgt ggattttcta gttagcttct   240
tcacagagaa cctcttggat ctattctaaa ccttatgaat ggcaagttat cgttgggaag   300
cattgataac ttgtgcacaa gtgtgaagaa tctcaaccca tcatggttca tcgggtcatg   360
aaacaaatcc tttctgatta atccaagggt cgctcctaaa tttggttgta agatcaatcc   420
actaaatgtt ttacaagaag acgacgctcc taagtattgg tgtggcactg tagcagataa   480
agataatgag ggacgtacaa tgatttcaaa gaaaaatgat atgctacaat atccagcaaa   540
aaaactgaaa cttttttgagc caaggtgttc tgatggagca aaagaagctg gtgtgggatt   600
tatgaagagg ccgtgtctat ttgttgtgat ggatgatctg aaagtgatac caatgacaac   660
tacttctagc attgagtatc tgcaaaagct ggaggaggag aatgtcgagt tgga          714

<210> SEQ ID NO 26
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 26
aatcccacac cagcttcttt t                                              21
```

```
<210> SEQ ID NO 27
<211> LENGTH: 26
<212> TYPE: DNA
<213> ORGANISM: Artificial Sequence
<220> FEATURE:
<223> OTHER INFORMATION: Primer/Probe/Target Sequence

<400> SEQUENCE: 27
gtgtggcact gtagcagata aagata                                              26

<210> SEQ ID NO 28
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 28
cagaacatct tggc                                                           14

<210> SEQ ID NO 29
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 29
cagaacacct tggc                                                           14

<210> SEQ ID NO 30
<211> LENGTH: 714
<212> TYPE: DNA
<213> ORGANISM: Glycine max

<400> SEQUENCE: 30
tttctgatat ttakcatact aaasgaagca ttaacctcca aatmtcctct tagtaatgta          60
ttcttagaaa atagagaatc taattcatca yactctttct catcacatac tggctcrgat         120
gcttgtggcc catttcattg gaaaggttct cyagaaatca agataatgtt wagcaaatca         180
aagarcraga ttctgtttgc tggagcagag ggagatttgt ggattttcta gttagcttct         240
tcacagagaa cctcttggat ctattctaaa ccttatgaat ggcaagttat cgttgggaag         300
cattgataac ttgtgcacaa gtgtgaagaa tctcaaccca tcatggttca tcgggtcatg         360
aaacaaatcc wtwctgatta atccaagggt cgctccyaaa tttggttgta agatcaatcc         420
actaaatgtt ttacaagaag acgacgctcc taagtattgg tgtggcactg tagcagataa         480
agataatgag ggmcgtacaa tgatttcaaa gawaaatkat atgctacaat atccagcaaa         540
aaamctgaaa cttttttgagc caagrtgttc tgatggagca aaagaagctg gtgtgggatt         600
tatgaaragg ccgtgtctat tgttgtgat ggatgatctg aaagtgatac caatgacaac          660
tacttctagc attgagtatc tgcaaaagct ggaggaggag aatgtcgagt tgga              714

<210> SEQ ID NO 31
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 31
tcatttcctg atgctcacca ta                                                  22
```

<210> SEQ ID NO 32
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 32
ggttgtatcc atcttctgaa ctgc                                          24

<210> SEQ ID NO 33
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 33
ttgagaaaac gtctgca                                                  17

<210> SEQ ID NO 34
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 34
ttgagaaaac atctgca                                                  17

<210> SEQ ID NO 35
<211> LENGTH: 466
<212> TYPE: DNA
<213> ORGANISM: Glycine max
<220> FEATURE:
<221> NAME/KEY: misc_feature
<222> LOCATION: (13)..(13)
<223> OTHER INFORMATION: n is a, c, g, or t

<400> SEQUENCE: 35
ttatgtaact tcnttttgta gcaggctaaa ttatcacatt gggacctacg agcgaaaaaa    60
gggtgaatct ctagctatac tatattatta ttttatttgt ttcccttcac tagttgattt   120
ggttgtatcc atcttctgaa ctgcttcaga tgctgcagat gctgccttgt ctagacctaa   180
cctttgcaac tcagttgaga aaacagtctg catctgtttt gctgattttg tatggactat   240
ggtgagcatc aggaaatgaa ccatttatca cgtcttcctt atactccagt aaggctttat   300
tgatgacatc tcctacacgt gcatactgct tacaaaattt tggagtaacc tgaaaaagat   360
acatcatctc aaaattagca atgaattcca taatgtctga agagaaaac aaggttagga    420 tatgctacaa ataccttcgc atggtgaggg catggtcata gctgtt                 466

<210> SEQ ID NO 36
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 36
tgtactttgg ctgcgtctcc                                               20

<210> SEQ ID NO 37

```
<211> LENGTH: 26
<212> TYPE: DNA
<213> ORGANISM: Artificial Sequence
<220> FEATURE:
<223> OTHER INFORMATION: Primer/Probe/Target Sequence

<400> SEQUENCE: 37
ggtaactcct ttgtaatgtt caccac                                         26

<210> SEQ ID NO 38
<211> LENGTH: 13
<212> TYPE: DNA
<213> ORGANISM: Artificial Sequence
<220> FEATURE:
<223> OTHER INFORMATION: Primer/Probe/Target Sequence

<400> SEQUENCE: 38
ccatgtcaat gcc                                                       13

<210> SEQ ID NO 39
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 39
ccatgtcaac gcca                                                      14

<210> SEQ ID NO 40
<211> LENGTH: 607
<212> TYPE: DNA
<213> ORGANISM: Glycine max

<400> SEQUENCE: 40
actttcatca aagaacaaa gcaaccgaat tttgacaccc aaatctggaa ttgacctgac      60
tgcaaacgac aacagtaaat attttcaatc tttgaagata tagaactcca atgttactaa    120
aaataaggct gtgaatgtta gtaatggaag taaaactacc ttttctcttg atataaaaag    180
agagtatatc tcaattgatg aggatgatcc agaaggcact aatgctttgc aaggatgttc    240
aaaacacaac tacaaagatc aagacaggga tgatattgct tttagcaagc cttcyctagt    300
gaagctagag yctgtgtctg cataaagac tgaaamatca ttgcaaggaa awtgtacttt     360
ggctgcgtct ccyagagttg atattgacat tggcrttgac atggctaaca tttcagctgg    420
tgctatggat gaagatgtaa ctttacaaac aacattaaa caacccgtgg tgaacattac     480
aaaggagtta ccattaacac tttcaaattc aggtatgcta ctagttgagt tttaaaaaca    540
gatttttttt aattaaaagt atatactatt catgatttac tgaacaaaac tcaaatkctg    600
ggcattt                                                              607

<210> SEQ ID NO 41
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 41
gctgctcttt ctctgctgtg atca                                           24

<210> SEQ ID NO 42
<211> LENGTH: 26
```

```
<212> TYPE: DNA
<213> ORGANISM: Artificial Sequence
<220> FEATURE:
<223> OTHER INFORMATION: Primer/Probe/Target Sequence

<400> SEQUENCE: 42
tgggtggttt ccttgtttat accaac                                            26

<210> SEQ ID NO 43
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 43
tatacccgtg agactat                                                      17

<210> SEQ ID NO 44
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 44
tataccggtg agactat                                                      17

<210> SEQ ID NO 45
<211> LENGTH: 441
<212> TYPE: DNA
<213> ORGANISM: Glycine max

<400> SEQUENCE: 45
tactgaagtg aatcgatact gtattcatca ataccgtgt aaataccacc gatctcgaaw         60
tgtctgaggt gcttgttttg agaattgtaa acatgaatwa tgtatacatg tgtgattcaa      120
ttaagaaacc aaataatggt attgagatgg agatgctctt atcctagtgt tggtggtccc      180
tttttaaaac aaaatttgca tttcaaataa actaaagatc aaaacaaaca gacacgggag      240
ataaggtctt ctccttctgt aaagkgcatg caacttgctg ctctttctct gctgtgatca      300
gtgtgaagat aatccaaaga aatttcaacg ttttaaataa aagggtaaga gttgaaactc      360
atagtctcac sggtataaaa aaatgctagt tggtataaac aaggaaacca cccacgcakg      420
gtcatagact atatacaacc a                                                441

<210> SEQ ID NO 46
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 46
ggcatttgct tcaattttcc                                                   20

<210> SEQ ID NO 47
<211> LENGTH: 23
<212> TYPE: DNA
<213> ORGANISM: Artificial Sequence
<220> FEATURE:
<223> OTHER INFORMATION: Primer/Probe/Target Sequence

<400> SEQUENCE: 47
```

```
acttttgccc ctatakgata tgc                                          23
```

<210> SEQ ID NO 48
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 48

```
actctggata acctg                                                   15
```

<210> SEQ ID NO 49
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 49

```
actctgggta acctg                                                   15
```

<210> SEQ ID NO 50
<211> LENGTH: 551
<212> TYPE: DNA
<213> ORGANISM: Glycine max

<400> SEQUENCE: 50

```
ggttcctttg taacttacca tctatctaga aactgcagga ttctcttgta aaataaaata    60
ttaaatgata taatacttga gatatgtagt tggctaaayt tcatcttata tgaggcattt   120
gcttcaattt tccagactat tgcctttacc ttctagactc tggrtaacct gaactgcata   180
tcmtataggg gcaaaagtat gttatttgt cagcatataa acatgtttgc atcctataca   240
gtcaagtatt ctacacagat actatagaaa gtagaaagaa tagtggtrct tttcacttgt   300
ttctgttgaa aactgaatac aaagatatag agagagtaga gagaaagggg agataaggtt   360
tctctgaaaa tgtctcaact ctttagatga tttcgtagag gtgttcacag attggatttg   420
attggttttg aggagtaaag ttattcaatc atatcccatt gttttatttt tatttaaaca   480
tccaatcaat ttgatcctaa attaaatatg atctaattca ttccaatcaa aagtgggttt   540
ggattggatc a                                                       551
```

<210> SEQ ID NO 51
<211> LENGTH: 26
<212> TYPE: DNA
<213> ORGANISM: Artificial Sequence
<220> FEATURE:
<223> OTHER INFORMATION: Primer/Probe/Target Sequence

<400> SEQUENCE: 51

```
agagagcaac aaccagtaat ttcata                                       26
```

<210> SEQ ID NO 52
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 52

```
acttagtgca tctattgcaa ccac                                         24
```

```
<210> SEQ ID NO 53
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 53
ccactaaagt tagcctag                                                  18

<210> SEQ ID NO 54
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 54
ccactaaggt tagcctag                                                  18

<210> SEQ ID NO 55
<211> LENGTH: 301
<212> TYPE: DNA
<213> ORGANISM: Glycine max

<400> SEQUENCE: 55
tagatctcct taatagttgg ttaattttc aataatgagt gtcacaattt accatcatag     60
agagcaacaa ccagtaattt catattgttt aggatgaaat aaaatgtttt actaagatcg   120
taatcaaaat ctaaatttgt tgcccactaa rgttagccta gcggtagcta gtggttgcaa   180
tagatgcact aagtgttacg atcgatsttc attgctatta ttctactaaa atcaaaatca   240
aaatttattt attttatata gactaaaaat atatttaaac aaattagtca tgtctgcata   300
g                                                                   301

<210> SEQ ID NO 56
<211> LENGTH: 23
<212> TYPE: DNA
<213> ORGANISM: Artificial Sequence
<220> FEATURE:
<223> OTHER INFORMATION: Primer/Probe/Target Sequence

<400> SEQUENCE: 56
ccttcaacaa cagcagcttt aat                                            23

<210> SEQ ID NO 57
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 57
ctgcttaatc gactgagcta gacc                                           24

<210> SEQ ID NO 58
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 58
cattagatca aacactgc                                                  18
```

<210> SEQ ID NO 59
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 59
cattagatca aacattgc                                                 18

<210> SEQ ID NO 60
<211> LENGTH: 301
<212> TYPE: DNA
<213> ORGANISM: Glycine max

<400> SEQUENCE: 60
atgcttcatt cctcccaggt atgatgttca actaatttat tgttctagt ttctgtttca    60 tatatggaac atggaaccct ctgactatcg ttaaagtcag ttagccttca acaacagcag  120
ctttaatctg tgtgcacatt agatcaaaca ytgcatttat ttcaattaat ctaaacaaag  180
aaaaaaatat gtatgtggtg gtacaataaa ctattgtgta acaatcaagg gggtctagct  240
cagtcgatta agcagagtat gtaagtatta taaattttct ggtagcgtgt ttaattccta  300
c                                                                  301

<210> SEQ ID NO 61
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 61
gcttgtaagc tattcccaaa cg                                            22

<210> SEQ ID NO 62
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 62
tatctgtgag cggttgcttg                                               20

<210> SEQ ID NO 63
<211> LENGTH: 19
<212> TYPE: DNA
<213> ORGANISM: Artificial Sequence
<220> FEATURE:
<223> OTHER INFORMATION: Primer/Probe/Target Sequence

<400> SEQUENCE: 63
tttcttatct aaggttttg                                                19

<210> SEQ ID NO 64
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 64
ttcttatcaa aggttttg                                                 18

```
<210> SEQ ID NO 65
<211> LENGTH: 650
<212> TYPE: DNA
<213> ORGANISM: Glycine max

<400> SEQUENCE: 65
acctgagcca cactatgagc taacatgaga attcatctaa tcatagtttg ygtgaaatct    60
gcttctggct acactaaata acttgaactg ctctctatta atggagttaa catgaaaaga   120
gtaaattgtt agcatttctt tattcaagta ttcatcaggt ctcttttctc aagttttcat   180
taatatggta tgaatgract gtttgttact atatctgtga gcggttgctt gcaacataaa   240
catgtacttg ctgttatgct actgctccta aagatatgta atttaattta gttatcaaaa   300
ccttwgataa gaaaatctgc gtttgggaat agcttacaag cttcttttgt agtcgttctg   360
acctattgts agggtagagt tacttactgg tgtatatcat ggttgatgga tgtgtaaatt   420
tctatgcagg tcattgatga ttttgctaag tttaatctgc ttctcaaagt caagagggga   480
cagaaggaag agaagtttaa ggtagaggta cacaagaata accaagggggg gttccatcta   540
aatcagatgg aacaagatca ttcctaattc tgatctgaag tttggtcacc ctagcaatat   600
tgttcttatc tatgtctagt gcttacccct ttctctgtgc cttggcaaat                650

<210> SEQ ID NO 66
<211> LENGTH: 26
<212> TYPE: DNA
<213> ORGANISM: Artificial Sequence
<220> FEATURE:
<223> OTHER INFORMATION: Primer/Probe/Target Sequence

<400> SEQUENCE: 66
tgaggatatt tatggaattt gtcaga                                          26

<210> SEQ ID NO 67
<211> LENGTH: 25
<212> TYPE: DNA
<213> ORGANISM: Artificial Sequence
<220> FEATURE:
<223> OTHER INFORMATION: Primer/Probe/Target Sequence

<400> SEQUENCE: 67
catgatgaga tcagaaaaga aatgc                                           25

<210> SEQ ID NO 68
<211> LENGTH: 17
<212> TYPE: DNA
<213> ORGANISM: Artificial Sequence
<220> FEATURE:
<223> OTHER INFORMATION: Primer/Probe/Target Sequence

<400> SEQUENCE: 68
cttataaaac cgctttc                                                    17

<210> SEQ ID NO 69
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 69
cttataaaac tgctttcc                                                   18
```

-continued

```
<210> SEQ ID NO 70
<211> LENGTH: 301
<212> TYPE: DNA
<213> ORGANISM: Glycine max

<400> SEQUENCE: 70
ccatgactgc aaattattga ttgcctattt attcaatctg atcctagtgg tgtagcttgt      60
tggttaagag ttgaggatat ttatggaatt tgtcagaaaa cttttcacat gtaaagttgt     120
agtataagga atcagacatt cttataaaac ygctttccat ttctagcttt gctggcattt    180
cttttctgat ctcatcatga tgtgaaaatt atactgacat gaaattttgg ccactgcttg    240
tgtgttcaaa aagctaaact tcacatacaa cattttggta acaaggttat ttgtgattgc    300
a                                                                    301

<210> SEQ ID NO 71
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 71
gacagtggag agttacgagg a                                               21

<210> SEQ ID NO 72
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 72
cacatctgaa tcaccctgga                                                 20

<210> SEQ ID NO 73
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 73
ccacctacat cactac                                                     16

<210> SEQ ID NO 74
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 74
ccacctacat gactac                                                     16

<210> SEQ ID NO 75
<211> LENGTH: 509
<212> TYPE: DNA
<213> ORGANISM: Glycine max
<220> FEATURE:
<221> NAME/KEY: misc_feature
<222> LOCATION: (49)..(52)
<223> OTHER INFORMATION: n is a, c, g, or t

<400> SEQUENCE: 75
```

```
tgtaactata tacaaaatat cacgaataac tccagcagga cctaatccnn nntgattgtt      60
acatacaaac aytacaatca cttaasgaac aacaaaactm taccagacat gatccaaaac     120
atccttaggc acccaaaagg aatgtaagct cyaactctaa cyttraaagg tcagaaggag     180
ttataagact caccagagtc actrgacagt ggagagttac gaggagaacc cccaatacca     240
cctacatsac tactatcaaa acctatggct tcaagccaaa aactaatcca gggtgattca     300
gatgtgtcac ctttcatgaa gatattgacc tgcatgttaa gagctcrccg cctcctgggt     360
gtgatatgct cttggttaag gacattatgg ggctccytat gtcccgtwcg atttstgttc     420
agttttcctg ggcattaagc cctcctcaga ataaaaaaaw gaaaaagaaa agaggatgtg     480
ccgcctctcg tccatggtca tagcctgtt                                        509
```

```
<210> SEQ ID NO 76
<211> LENGTH: 25
<212> TYPE: DNA
<213> ORGANISM: Artificial Sequence
<220> FEATURE:
<223> OTHER INFORMATION: Primer/Probe/Target Sequence

<400> SEQUENCE: 76
tctttatgat gatgagcaga agcta                                            25

<210> SEQ ID NO 77
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 77
caccccaaaa acaaaacact c                                                21

<210> SEQ ID NO 78
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 78
ctttcagagc attagc                                                      16

<210> SEQ ID NO 79
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 79
tttgctttca gggcat                                                      16

<210> SEQ ID NO 80
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 80
gggaagagtc tgaatggtgt ct                                               22
```

```
<210> SEQ ID NO 81
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 81
ccccaaaaac aaaacactca tc                                              22

<210> SEQ ID NO 82
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 82
ctttcagagc attagc                                                     16

<210> SEQ ID NO 83
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 83
tttgctttca gggcat                                                     16

<210> SEQ ID NO 84
<211> LENGTH: 625
<212> TYPE: DNA
<213> ORGANISM: Glycine max

<400> SEQUENCE: 84
taaatatgaa yattttttctc aataaaaatw aataarcttg aatcaatgtt ccaacacgag     60
ttacattaca acttayaaac accatctaac gttctaagta gaggttttg agagttatca     120 cctggcaaga agtagctgtg tctggaaaag ctgctgttgg agcagaaatc acaatacaca    180
aaacccataa cactgatttg tgagatgggg aacctggttt tcccaggaag cttggttctt    240
gcaggctcaa cttccaaaaa ctgagtaaaa aagggaaaaa gaagcaagag ggttatggta    300
ttcatggcca actttgttaa aaaaaaatgg agggaagagt ctgaatggtg tctttatgat    360
gatgagcaga agctagagct tttgctttgt tttgctttgc tttcagrgca ttagcattta    420
gctgctagta gaagaaaatg atgagtgttt tgttttggg gtgtggataa agaggggcag     480
tggttagtgg agaaccaact tcaagcaaaa agttggaaat atttttttct tttcttttt     540 tcacaagaaa caaagacatg tgaatgttgt ttggcatrac atggagctca tgagtaggag    600
agagaagggg taagcagatt ytttt                                          625

<210> SEQ ID NO 85
<211> LENGTH: 25
<212> TYPE: DNA
<213> ORGANISM: Artificial Sequence
<220> FEATURE:
<223> OTHER INFORMATION: Primer/Probe/Target Sequence

<400> SEQUENCE: 85
tctgatgatg attatagtgg gctct                                           25
```

```
<210> SEQ ID NO 86
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 86
tgctatgcat ttgaaaccac a                                             21

<210> SEQ ID NO 87
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 87
ctgataacaa tagccc                                                   16

<210> SEQ ID NO 88
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 88
ataacaacag ccctgact                                                 18

<210> SEQ ID NO 89
<211> LENGTH: 752
<212> TYPE: DNA
<213> ORGANISM: Glycine max
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 89
catgrmyttg agataggttg caaaggctta gagnagagtt atggctaaaa gtgagatgaa    60
attcatngga gtagtgattc tgatgatgat tatagtgggc tctacacaag ctgataacaa   120
yagccctgac ttgactgggt gtgaagttaa atgtggtttc aaatgcatag catatttcta   180
tagtaaaaaa aaatttgacg aatgttgtct cccttgtatt cgaaaatgtc atcatgaaat   240
gtccattgat gttgtytatg attgcattac tggttgccgc ttaaccaagt ccattgatga   300
caacattggt atttatcctt ttgcaaaact tttattaagt tttattttta taattaagtt   360
aattatgttt tcacatgttt ttttattatt gactttacat gtcagatgct cgtgttctta   420
ccgttcatgc aatggattct tgtgtgcaag agtgcaagaa caagtaagag tttgttgcaa   480
aaatgctcag aaaaaaatat tagttggaga ataatatgt atccatgttt gtaataaata    540
attcttaata aatatgtaat atctcatctt tattttccgt aaatcttttg tccaattatt   600
tttcttgatt tgtctgatgt tcctgtcata cctgagcaaa taatcatgct tctaaattaa   660
attaataatg acactaataa ttttattata tccaaatgga aaatgtatgc acaaaaaata   720
ttgatgacca atatattaaa agttgagaaa tt                                 752

<210> SEQ ID NO 90
```

```
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 90
ggacccaaca tcaatcaaat g                                              21

<210> SEQ ID NO 91
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 91
tgcattctgg aaagacatgg                                                20

<210> SEQ ID NO 92
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 92
ttttctgcac tccc                                                      14

<210> SEQ ID NO 93
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 93
ttttctggac tccc                                                      14

<210> SEQ ID NO 94
<211> LENGTH: 120
<212> TYPE: DNA
<213> ORGANISM: Glycine max

<400> SEQUENCE: 94
ttctcatggc tttctggttt gcattctgga aagacatggg catgaaacaa taatgggagt    60
scagaaaaca caacccctt ataattctct cacaactatc atttgattga tgttgggtcc    120

<210> SEQ ID NO 95
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 95
catgccagta tgaatgtgct g                                              21

<210> SEQ ID NO 96
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 96
```

```
tccgcacatt tagttccctt a                                              21

<210> SEQ ID NO 97
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 97
attgtgacac tctattgc                                                  18

<210> SEQ ID NO 98
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 98
ttgtgacact ctatggca                                                  18

<210> SEQ ID NO 99
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 99
caaagtgtca tgccagtatg aatg                                           24

<210> SEQ ID NO 100
<211> LENGTH: 26
<212> TYPE: DNA
<213> ORGANISM: Artificial Sequence
<220> FEATURE:
<223> OTHER INFORMATION: Primer/Probe/Target Sequence

<400> SEQUENCE: 100
gttttatttt cattccgcac atttag                                         26

<210> SEQ ID NO 101
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 101
attgtgacac tctattgc                                                  18

<210> SEQ ID NO 102
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 102
ttgtgacact ctatggca                                                  18

<210> SEQ ID NO 103
<211> LENGTH: 576
<212> TYPE: DNA
```

```
<213> ORGANISM: Glycine max
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (570)..(571)
<223> OTHER INFORMATION: n is a, c, g, or t

<400> SEQUENCE: 103
aaaaggctat gaccatgttt ttcaggggtc ctggtgtaac tgtactaatc ctgtcatgga    60
tcatcaccct gtacactcta tggcaaatgg ttgagatgca tgaaatggta cctggaaaac   120
gttttgatag gtatcatgaa ctggggcagt atgcctttgg ggagaagcta ggactttata   180
tagtggtgcc tcaacaactt gtggtggaaa ttggggtgaa cattgtctat atggttactg   240
ggggaaaatc cttgcaaaag ttccatgaca ctgtrtgtga cagctgcaaa aagatcaagt   300
tgaccttttt cattatgatc tttgcctctg ttcactttgt actgtctcac ctgcccaact   360
tcaactccat ttttggtgta tctntggcag cagcagttat gtccttgagg tacaagtcat   420
aaccttttag ttatataggt ttaattaaac ttttggtcct cgtttattt tcattccgca    480 catttagttc cctattttt ttttcctaca aatttgatct yttactgtta attttgatca    540
atctattgtg acactctatk gcactattan ntcrsm                             576

<210> SEQ ID NO 104
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 104
gatcggttcc caaactagca                                                20

<210> SEQ ID NO 105
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 105
aacatgcaaa atgcaccaag                                                20

<210> SEQ ID NO 106
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 106
cagttgatta ctctgc                                                    16

<210> SEQ ID NO 107
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 107
cagttgatta ctttgc                                                    16
```

<210> SEQ ID NO 108
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 108
cggttcccaa actagcaggt                                                    20

<210> SEQ ID NO 109
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 109
tgcaaaatgc accaagttag at                                                 22

<210> SEQ ID NO 110
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 110
agatcggttc ccaaactagc ag                                                 22

<210> SEQ ID NO 111
<211> LENGTH: 21
<212> TYPE: DNA
<213> ORGANISM: Artificial Sequence
<220> FEATURE:
<223> OTHER INFORMATION: Primer/Probe/Target Sequence

<400> SEQUENCE: 111
catgcaaaat gcaccaagtt a                                                  21

<210> SEQ ID NO 112
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 112
cagttgatta ctctgc                                                        16

<210> SEQ ID NO 113
<211> LENGTH: 16
<212> TYPE: DNA
<213> ORGANISM: Artificial Sequence
<220> FEATURE:
<223> OTHER INFORMATION: Primer/Probe/Target Sequence

<400> SEQUENCE: 113
cagttgatta ctttgc                                                        16

<210> SEQ ID NO 114
<211> LENGTH: 480
<212> TYPE: DNA
<213> ORGANISM: Glycine max

<400> SEQUENCE: 114

```
tccatctaag tctacaactc tttccacatc ttagaagacc ttcaccaaca tgcaaaatgc    60
accaagttag atacatatat atcatatcat accccttaat ttattgcara gtaatcaact   120
gtagaacatg tgaacacgac ttttaataaa ctaacttatt acctgctagt ttgggaaccg   180
atctccagca atggatacca ttgttgagaa taaagttcat gagcttgtga tcctcctcaa   240
tagtccatgg acctctcttc aaaccaacct tatcacaaca aggttgtctt cccattttgt   300
aagcctttc ttttctttga gaaatcaaga caaatatatc ccttgatata gaaagttact   360
aatawcaagt gtgaaacmtt ggaagcatga cacttaaaaa ggagcttgag attgaagcaa   420
agatgctgcc agttcattca aacatttaaa taaaagcatg atgtcctttg aggggggaga   480
```

<210> SEQ ID NO 115
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 115

```
ccaccattac ccctctcctt                                                20
```

<210> SEQ ID NO 116
<211> LENGTH: 22
<212> TYPE: DNA
<213> ORGANISM: Artificial Sequence
<220> FEATURE:
<223> OTHER INFORMATION: Primer/Probe/Target Sequence

<400> SEQUENCE: 116

```
acctagcatt gcaatctctt cc                                             22
```

<210> SEQ ID NO 117
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 117

```
ttggcattca gccc                                                      14
```

<210> SEQ ID NO 118
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 118

```
tttggcattc acccc                                                     15
```

<210> SEQ ID NO 119
<211> LENGTH: 25
<212> TYPE: DNA
<213> ORGANISM: Artificial Sequence
<220> FEATURE:
<223> OTHER INFORMATION: Primer/Probe/Target Sequence

<400> SEQUENCE: 119

```
ttacccctct cctttctcaa catta                                          25
```

<210> SEQ ID NO 120
<211> LENGTH: 24
<212> TYPE: DNA
<213> ORGANISM: Artificial Sequence
<220> FEATURE:
<223> OTHER INFORMATION: Primer/Probe/Target Sequence

<400> SEQUENCE: 120
tgcaatctct tccaagctag aact                                          24

<210> SEQ ID NO 121
<211> LENGTH: 763
<212> TYPE: DNA
<213> ORGANISM: Glycine max
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (754)..(755)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t

<400> SEQUENCE: 121
atctatcttc aatccanatc tacaaaaact tagatccaca aaatmmanat atgcaaaacc    60
aaaaatgacg atggtgaatg gtggtgtcgc gatccaaaac ccgtggcggt ggtttaacgg   120
aatggtggtg ggggaaaact ggtaagggtt cacactttca cgttgggtac caaaagggca   180
caaatctggt tctatggggg gggcatttta gttctccgtc ggtggtgaag ggtggtgtca   240
caatggcaag cgtgtctggt ttttttttcac tgtcgcttcg agaatcccgt caatttgctc   300
ttcactatcg ctttcagatt tcactcatag tgcattcttt ctgtcgatgt gtcactctcc   360
acctagcatt gcaatctctt ccaagctaga actagaattt agatgtgcat atctcaaagt   420
ttgaagcaga aatctgagac gatgggstga atgccaaatt ttttgttgca ataatgttga   480
gaaaggagag gggtaatggt gggcaggggt tgaaaaactg aaaaattgag tgtaaaccga   540
aaaccaacca aaaaaccaca aactacaaaa aaaatcgaag agcattgatt tagttttggtt  600 tttgttttcc caaccgagcg ggttgattca attttttggtt taacatgcaa aaattgaayc   660
aaaccaaatc gaactgcact ygttagttta agtttaatta ttataggact caagactcat   720
gcatactaca tgtagtttaa gtttaagctt atgnntnaac gac                     763

<210> SEQ ID NO 122
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 122
aggtggtggc agtgttgatt                                               20

<210> SEQ ID NO 123
<211> LENGTH: 20
<212> TYPE: DNA
<213> ORGANISM: Artificial Sequence
<220> FEATURE:

<223> OTHER INFORMATION: Primer/Probe/Target Sequence

<400> SEQUENCE: 123
ctccaacatg gctgtgctaa                                                    20

<210> SEQ ID NO 124
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 124
aaccgtggct catt                                                          14

<210> SEQ ID NO 125
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 125
caaaccgtgg cttat                                                         15

<210> SEQ ID NO 126
<211> LENGTH: 467
<212> TYPE: DNA
<213> ORGANISM: Glycine max

<400> SEQUENCE: 126
yggaaaatga taagccccca acctgtgttt gttggggaa aattaggtgm atttctgtac          60
tggtaattgg ttttaaattt taatccaatt tcccttattc tgttactaga ttaaagggat        120
tgacagacat gcaaaaatgt ggaggaaaag gtgtgttttt cagagcattt gggccttcct        180
aacttgattt cagcccctgg acctccaaca tggctgtgct aaagcttgg agcaccttgg         240
aaaaatatct tgtttggaa atagcatgtt tgtgctagaa tttacatgac tgcrtttaat        300
agagccacgg tttggttatt aatcaacact gccaccacct gccccctgttt ttgtaattct      360
gactcagttg tgtgctatt aagcctgtca attgacctag ggctggactt ttggttgctg        420
ttgacacatt ctraasgttt tcttgagttc tcaaccgttt tctaggg                     467

<210> SEQ ID NO 127
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 127
ttcagctccc cattatttcg                                                    20

<210> SEQ ID NO 128
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 128
ttggccaacc tatcctcaac                                                    20

```
<210> SEQ ID NO 129
<211> LENGTH: 15
<212> TYPE: DNA
<213> ORGANISM: Artificial Sequence
<220> FEATURE:
<223> OTHER INFORMATION: Primer/Probe/Target Sequence

<400> SEQUENCE: 129
tcagctcatt tttgt                                                    15

<210> SEQ ID NO 130
<211> LENGTH: 14
<212> TYPE: DNA
<213> ORGANISM: Artificial Sequence
<220> FEATURE:
<223> OTHER INFORMATION: Primer/Probe/Target Sequence

<400> SEQUENCE: 130
cagctcactt ttgt                                                     14

<210> SEQ ID NO 131
<211> LENGTH: 548
<212> TYPE: DNA
<213> ORGANISM: Glycine max
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

<400> SEQUENCE: 131
tggcttctag ganataacac atgttatttg aaggaataat aataatccta ctcannnatn    60
nagtcgactt cagctcccca ttatttcgca gctccatcac aatatcatga ccaccaatca   120 gctcayttttt gtagtagagt tgaggatagg ttggccaatt tgagtatacc ttcaatccct  180
gtctcacttc ctcatcagtc aatatatcaa aggacccaaa attcaagccc tcttgtcgaa   240
gggcatcagc aactctggaa ctaaaaccac atcttggtgc atctggggta cccttcatga   300
acagcatcac aggggacgag gcaatcaaat tcttcagtcg atcttgaatg gtctctgcag   360
gaagaatccc tttctcgtgt aaattcttcy taagttctcc gcttttttgc atctccaaca   420
caatatctga tccaccaata agctcaccct tgatatacag ttgaggataa ctggaccagt   480
ttgaataaac cttaagccct tgacgaactt cttcatcagt aagaatgtca aaactctcaa   540
agggaaca                                                            548

<210> SEQ ID NO 132
<211> LENGTH: 25
<212> TYPE: DNA
<213> ORGANISM: Artificial Sequence
<220> FEATURE:
<223> OTHER INFORMATION: Primer/Probe/Target Sequence

<400> SEQUENCE: 132
ccaaatcaga tatcaagatg atggt                                         25

<210> SEQ ID NO 133
<211> LENGTH: 21
<212> TYPE: DNA
```

```
<213> ORGANISM: Artificial Sequence
<220> FEATURE:
<223> OTHER INFORMATION: Primer/Probe/Target Sequence

<400> SEQUENCE: 133
ggccaagcaa tacacaagaa a                                              21

<210> SEQ ID NO 134
<211> LENGTH: 18
<212> TYPE: DNA
<213> ORGANISM: Artificial Sequence
<220> FEATURE:
<223> OTHER INFORMATION: Primer/Probe/Target Sequence

<400> SEQUENCE: 134
atctatgatt ccattttt                                                  18

<210> SEQ ID NO 135
<211> LENGTH: 20
<212> TYPE: DNA
<213> ORGANISM: Artificial Sequence
<220> FEATURE:
<223> OTHER INFORMATION: Primer/Probe/Target Sequence

<400> SEQUENCE: 135
atcatctatg tttccatttt                                                20

<210> SEQ ID NO 136
<211> LENGTH: 401
<212> TYPE: DNA
<213> ORGANISM: Glycine max

<400> SEQUENCE: 136
tgaaccatat cgggtacata atgaaaccgc cgaataattc ccaagtgttt ggtagcaaca     60
tcaacaccaa tgagatcatc gagagtgaac caaacatcag catgagagtt tcaaagtgat   120
gaacccttac tatgggaatg gcatacttcy gccgcctgcc ccagaaggcc aagcaataca   180
caagaaagct aaaaatggaa wcatagatga tctttggatg aacatgaaat gkggtgggac   240
catcatcttg atatctgatt tggagaaaag taagaagtac aatatagatg aaagtatcaa   300
gggcatgcag aggatcggtt tctattgcca tgttaagttc ttggatatag agaacattga   360
aggtcacttc agtacctctg aaagcacagt taaaagaagt g                       401
```